United States Patent
Corak et al.

(10) Patent No.: US 8,626,337 B2
(45) Date of Patent: Jan. 7, 2014

(54) METHOD AND COMPUTER PROGRAM PRODUCT FOR DISTINGUISHING AND SORTING SEEDS CONTAINING A GENETIC ELEMENT OF INTEREST

(75) Inventors: Steven J. Corak, Johnston, IA (US); James L. Hunter, Maxwell, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 923 days.

(21) Appl. No.: 12/108,198

(22) Filed: Apr. 23, 2008

(65) Prior Publication Data
US 2009/0032441 A1 Feb. 5, 2009

Related U.S. Application Data

(60) Provisional application No. 60/913,562, filed on Apr. 24, 2007.

(51) Int. Cl.
*B07C 5/34* (2006.01)

(52) U.S. Cl.
USPC ........... 700/224; 209/577; 209/580; 800/282; 800/278; 800/287; 800/288; 800/303; 435/4; 435/6.16; 600/1

(58) Field of Classification Search
USPC .................. 700/219, 223, 224; 209/3.3, 577; 800/278–303
See application file for complete search history.

(56) References Cited

U.S. PATENT DOCUMENTS

| | | | |
|---|---|---|---|
| 2,152,758 A | 4/1939 | Cox | |
| 4,368,591 A | 1/1983 | Barke et al. | |

(Continued)

FOREIGN PATENT DOCUMENTS

| | | |
|---|---|---|
| CN | 1485803 A | 3/2004 |
| EP | 0 130 715 A2 | 1/1985 |

(Continued)

OTHER PUBLICATIONS

Office Action from related Chinese Patent Application No. 200880021834.3, issued Jan. 20, 2011.

(Continued)

*Primary Examiner* — Gene Crawford
*Assistant Examiner* — Kyle Logan
(74) *Attorney, Agent, or Firm* — Pioneer Hi-Bred International, Inc.

(57) ABSTRACT

A method and computer program product for distinguishing and sort seeds containing a genetic element of interest from a bulk sample. In various embodiments, the present invention comprises associating a marker with at least some of the seeds containing a genetic element of interest of the bulk sample, exciting the seeds using an electromagnetic energy emitting device, evaluating at least some of the seeds of the bulk sample for the presence or absence of the marker using an evaluating device configured to excite a majority of the surface area of the seeds, and sorting the seeds containing a genetic element of interest based on the presence or absence of the marker. In various other embodiments, the method and computer program product may comprise associating a red fluorescent protein marker with at least some of the seeds containing a genetic element of interest of the bulk sample, evaluating at least some of the seeds of the bulk sample for the presence of the red fluorescent protein marker using an evaluating device, and sorting the seeds containing a genetic element of interest based on the presence of the red fluorescent protein marker. In some embodiments, the red fluorescent protein marker is discernable when excited by a certain energy and the evaluating step comprises exciting the seeds containing a genetic element of interest with the certain energy detecting an emission resulting at least in part from the exciting step.

43 Claims, 10 Drawing Sheets

(56) References Cited

U.S. PATENT DOCUMENTS

| | | | |
|---|---|---|---|
| 4,630,736 A | 12/1986 | Maughan et al. | |
| 4,635,215 A | 1/1987 | Friend | |
| 4,723,661 A | 2/1988 | Hoppmann et al. | |
| 4,975,364 A | 12/1990 | Taylor et al. | |
| 5,412,219 A | 5/1995 | Chappelle et al. | |
| 5,441,735 A | 8/1995 | Takahara et al. | |
| 5,550,318 A * | 8/1996 | Adams et al. | 800/300.1 |
| 5,616,082 A * | 4/1997 | Kobetsky | 470/49 |
| 5,703,784 A * | 12/1997 | Pearson | 700/223 |
| 5,746,022 A | 5/1998 | Brown et al. | |
| 5,750,340 A | 5/1998 | Kim et al. | |
| 5,862,919 A * | 1/1999 | Eason | 209/577 |
| 5,865,990 A | 2/1999 | Novak et al. | |
| 5,916,029 A | 6/1999 | Smith et al. | |
| 5,929,307 A * | 7/1999 | Hodges et al. | 800/303 |
| 5,973,286 A | 10/1999 | Wan | |
| 6,022,689 A | 2/2000 | Sarto et al. | |
| 6,080,950 A | 6/2000 | Jalink | |
| 6,156,699 A | 12/2000 | Johnson et al. | |
| 6,307,123 B1 * | 10/2001 | Kriz et al. | 800/282 |
| 6,433,252 B1 * | 8/2002 | Kriz et al. | 800/287 |
| 6,627,799 B1 * | 9/2003 | Mariani et al. | 800/303 |
| 6,635,840 B1 * | 10/2003 | Mailloux | 209/586 |
| 6,646,264 B1 | 11/2003 | Modiano et al. | |
| 6,706,989 B2 | 3/2004 | Hunter et al. | |
| 6,734,383 B1 | 5/2004 | Calcoen et al. | |
| 6,865,556 B2 | 3/2005 | Penner et al. | |
| 6,936,827 B1 | 8/2005 | Mohler | |
| 6,947,144 B2 | 9/2005 | Kim et al. | |
| 7,073,653 B2 | 7/2006 | Hibari | |
| 7,086,269 B2 | 8/2006 | Sauder et al. | |
| 7,591,374 B2 | 9/2009 | Hunter et al. | |
| 7,703,238 B2 | 4/2010 | Deppermann et al. | |
| 2001/0053958 A1 | 12/2001 | Ried et al. | |
| 2002/0144458 A1 | 10/2002 | Hunter et al. | |
| 2003/0005626 A1 | 1/2003 | Yoneda et al. | |
| 2003/0135888 A1 * | 7/2003 | Zhu et al. | 800/288 |
| 2003/0142852 A1 | 7/2003 | Lu et al. | |
| 2003/0148258 A1 | 8/2003 | Kim et al. | |
| 2003/0233670 A1 * | 12/2003 | Edgerton et al. | 800/278 |
| 2004/0034268 A1 * | 2/2004 | Dell et al. | 600/1 |
| 2004/0118754 A1 * | 6/2004 | Hunter et al. | 209/577 |
| 2004/0205839 A1 * | 10/2004 | Doutriaux et al. | 800/278 |
| 2005/0032033 A1 | 2/2005 | Winterboer et al. | |
| 2005/0114923 A1 * | 5/2005 | Blaylock et al. | 800/282 |
| 2005/0224510 A1 | 10/2005 | Remis et al. | |
| 2006/0032421 A1 | 2/2006 | Sauder et al. | |
| 2006/0042528 A1 * | 3/2006 | Deppermann | 111/171 |
| 2006/0046244 A1 * | 3/2006 | Deppermann | 435/4 |
| 2006/0112628 A1 | 6/2006 | Kotyk et al. | |
| 2007/0077572 A1 * | 4/2007 | Tawfik et al. | 435/6 |
| 2007/0261939 A1 * | 11/2007 | Charpentier | 198/540 |
| 2008/0034652 A1 | 2/2008 | Hunter et al. | |
| 2008/0035532 A1 | 2/2008 | Hunter et al. | |
| 2008/0179226 A1 | 7/2008 | Hunter et al. | |
| 2008/0226753 A1 | 9/2008 | Cosgrove | |
| 2008/0244765 A1 | 10/2008 | Zhao et al. | |
| 2008/0289061 A1 | 11/2008 | Penner et al. | |
| 2008/0310674 A1 | 12/2008 | Modiano et al. | |
| 2008/0317279 A1 | 12/2008 | Deppermann et al. | |
| 2009/0032441 A1 | 2/2009 | Corak et al. | |
| 2009/0041869 A1 | 2/2009 | Cosgrove | |
| 2009/0119986 A1 | 5/2009 | Hunter et al. | |
| 2009/0260281 A1 | 10/2009 | Conrad | |
| 2010/0143906 A1 | 6/2010 | Becker et al. | |
| 2010/0281771 A1 | 11/2010 | Kudo et al. | |
| 2011/0202169 A1 | 8/2011 | Koehler et al. | |

FOREIGN PATENT DOCUMENTS

| | | |
|---|---|---|
| GB | 954333 | 4/1964 |
| JP | 63143087 | 6/1988 |
| JP | 10-309538 A | 11/1998 |
| WO | WO-85/00122 A1 | 1/1985 |
| WO | WO-2008/080166 A2 | 7/2008 |
| WO | WO-2008/085729 A2 | 7/2008 |
| WO | WO-2008/134347 A2 | 11/2008 |

OTHER PUBLICATIONS

"Optical Sorter,"<http://www.midwestseed.com/seervices/optical_sorter.asp>, printed Dec. 28, 2006.

"Satake Vision Systems,"<http://www.satake-usa.com/pdf/SMII_scanmaster_sorter%20.pdf>, printed Dec. 27, 2006.

International Search Report and Written Opinion for Application No. PCT/US2010/051078 dated Mar. 24, 2011.

International Search Report and Written Opinion for International Appl. No. PCT/US2008/061238, mailed Dec. 12, 2008.

Wenck et al., "Reef-Coral Proteins as Visual, Non-Destructive Reporters for Plant Transformation," *Plant Cell Reports*, vol. 22, No. 4, Nov. 1, 2003, pp. 244-251.

Melamed-Bessudo et al., "A New Seed-Based Assay for Meiotic Recombination in *Arabidopsis thaliana*," *The Plant Journal*, vol. 43, No. 3, Aug. 2005, pp. 458-466.

Stuitje et al., "Seed-Expressed Fluorescent Proteins as Versatile Tools for Easy (Co)transformation and High-Throughput Functional Genomics in *Arabidopsis*," *Plant Biotechnology Journal*, vol. 1, 2003, pp. 301-309.

Nishizawa et al., "A Red Fluorescent Protein, DsRed2, as a Visual Reporter for Transient Expression and Stable Transformation in Soybean," *Plant Cell Reports*, vol. 25, No. 12, Jul. 14, 2006, pp. 1355-1361.

Jach et al., "Use of Red Fluorescent Protein from *Discosoma* sp. (dsRED) as a Reporter for Plant Gene Expression," *The Plant Journal*, vol. 28, No. 4, 2001, pp. 483-491.

Partial International Search Report for International Appl. No. PCT/US2008/061238, mailed Sep. 25, 2008.

International Search Report and Written Opinion of the International Searching Authority for Application No. PCT/US2011/066084, dated Aug. 24, 2012.

Grainger: Laser Glasses, Red, [online] [retrieved Nov. 13, 2008]; Retrieved from internet: <URL: http://www.grainger.com/Grainger/wwg/search.shtml?searchQuery=3xa22&op=search&Ntt=3xa22&N=0&GlobalSearch=true&sst=subset > pp. 1-2.

International Preliminary Report and Written Opinion for Application No. PCT/US2011/066084; dated Jun. 25, 2013.

* cited by examiner

METHOD AND COMPUTER PROGRAM PRODUCT FOR DISTINGUISHING AND SORTING SEEDS CONTAINING A GENETIC ELEMENT OF INTEREST

CROSS REFERENCE TO RELATED APPLICATIONS

The present application claims priority from U.S. Provisional Application No. 60/913,562, filed Apr. 24, 2007, which is hereby incorporated herein in its entirety by reference.

FIELD OF THE INVENTION

The various embodiments of the present invention relate generally to a method and computer program product for distinguishing and sorting seeds that contain genetic elements of interest from seeds that do not. More specifically, embodiments of the present invention are capable of distinguishing and sorting the seeds containing the genetic elements of interest by detecting the presence of one or more discernable markers that are linked to one or more corresponding genetic elements of interest.

BACKGROUND OF THE INVENTION

Genetic engineering involves inserting new genetic information into existing cells of an organism to create a new genotype in order to modify the organism for the purpose of changing one or more of its characteristics. A living organism may be genetically engineered for a variety of reasons, including incorporating novel and/or beneficial traits into the organism. With regard to crop plants, this may include genetically engineering seeds so that plants that grow from the seeds include one or more beneficial traits. Such genetic engineering may include, but is not limited to, inserting genes encoding a discernable marker or genes conferring resistance to herbicidal compounds. The progeny of individual genetically modified organisms may also contain a genetic element of interest such that researchers may wish to segregate and/or identify organisms (including seeds) that contain such genetic elements of interest from a bulk sample.

Conventional genetic techniques may also be used to combine traits from at least two organisms to produce novel and/or beneficial traits in a "genetic cross" and/or hybrid organism.

It is often difficult to determine whether a particular seed contains a genetic element of interest, especially when mixed with seeds that have not been so modified. Using previous techniques, a particular seed would have to be germinated and then the resulting plant sampled to determine whether the seed might contain the genetic element of interest. Alternatively, the seed itself would have to be sampled.

There are advantages, however, in distinguishing a set of seeds containing a genetic element of interest before the respective plants are germinated, especially in the plant research discipline, where research plot space, personnel for sorting, and time are often limited. In maize and other wind-pollinated crops, plants are frequently hand-pollinated, wherein pollen is manually transferred from the tassel to the silk, and the silk is covered by a shoot bag to prevent pollination by other plants. This hand pollination process requires significant labor and a tassel bag and shoot bag. The prior elimination of undesired plants (i.e. plants that do not contain a genetic element of interest) by sorting seed may eliminate the need for this labor and time-intensive activity. Additionally, researchers may be interested in the yield potential of the plants germinated from seeds containing the genetic element of interest. Thus, it is important that a statistically-significant number of plants germinate from seeds containing the genetic element of interest in a defined space (i.e. a research plot). Furthermore, researchers desire accuracy and often cannot afford to wait or guess to determine whether plants contain a particular genetic element of interest. Additionally, seed and/or seed tissue sampling is a delicate art. For example, if too much tissue is removed from a particular seed for sampling, there is a risk that the seed may not germinate or produce a viable plant.

Some processes have been disclosed for visualizing green fluorescent protein (GFP) expression in transgenic plants in order to select transgenic seeds as described, for example, in U.S. Pat. No. 6,947,144 to Kim et al. In particular, the Kim reference describes a system for separating seeds transformed with a green fluorescent protein (GFP) that includes a light source 5' filtered through a bandpass filter 6'. The light source 5' is positioned above and at a 45° angle from plant samples traveling on a conveyor belt 3'. A CCD camera 9' is also positioned above the conveyor belt 3', directly above the examined plant sample 4'. The CCD camera 9' detects light generated from a portion of the surface area of the plant sample through a filter 7'. See, e.g., the Kim reference, FIG. 9.

However, the system disclosed by the Kim reference suffers from several insufficiencies. For example, there are a number of different traits, including the expression of fluorescent proteins, for which the accurate measurement of a seed in more than a portion of the surface area of the seed may be important. In some instances, the expression of a fluorescent protein may not be uniform across entire surface area of a seed. Thus, if a localized area of the seed expresses the fluorescent protein and that area is facing downward (such as against the conveyor belt in the Kim reference) the CCD camera will not detect the fluorescent protein and the seed will not be correctly sorted.

In addition, the use of GFP for identification and/or selection of transgenic plant material presents several technical challenges. First of all, the excitation and emission wavelengths for GFP visualization are on the fringes of the visible spectrum, and are therefore not easily visible to the eye (or to many conventional visualization systems) using normal "white" light that is present in conventional research and/or manufacturing environments. Furthermore, it has been noted that GFP may result in protein aggregation in vivo in plant material that has been tagged with GFP. It is well-known that unchecked protein aggregation may not only produce adverse effects in seed product, but may also produce unwanted environmental effects if GFP-tagged seeds are introduced into an agricultural environment that interacts with external ecological systems (such as forests and/or wetlands adjacent to an agricultural research plot).

As a result, there is a need for a method and computer program product for distinguishing seeds that contain a marker associated with a selected genotype from a bulk sample of seeds. The method and computer program product should permit a bulk sample to be sorted based on the presence of the marker or the absence of the marker, and should provide a level of convenience, accuracy, speed and environmental safety that is not available using conventional techniques. Additionally, the method and computer program product should provide the ability to accurately sort a bulk sample of seeds based on the presence or absence of markers associated with a selected genotype using commercially-available high-speed sorting equipment with minimal modifications.

SUMMARY OF THE INVENTION

The embodiments of the present invention satisfy the needs listed above and provide other advantages as described below. Some embodiments of the present invention may include a method for distinguishing seeds containing a genetic element of interest from a bulk sample by associating a discernable marker with at least some of the seeds containing a genetic element of interest of the bulk sample, evaluating at least some of the seeds of the bulk sample for the presence or absence of the marker using an evaluating device, and sorting the seeds containing a genetic element of interest based on the presence or absence of the marker.

In some embodiments the seeds are excited using an electromagnetic energy emitting device configured to excite a majority of the surface area of the seeds. In some embodiments, exciting the seeds using an electromagnetic energy emitting device comprises exciting the seeds using at least one illuminating device configured to illuminate a majority of the surface area of the seeds. In some embodiments, exciting the seeds using at least one illuminating device further comprises using two or more illuminating devices arranged to collectively illuminate a majority of the surface area of the seeds. In some embodiments, evaluating at least some of the seeds of the bulk comprises evaluating at least some of the seeds of the bulk sample using at least one image sensing device arranged to receive emissions from a majority of the surface area of the seeds. In some embodiments, evaluating at least some of the seeds of the bulk sample further comprises using two or more image sensing devices arranged to collectively receive emissions from a majority of the surface area of the seeds.

Other embodiments of the present invention may include a method and computer program product for distinguishing seeds containing a genetic element of interest from a bulk sample by associating a discernable red fluorescent protein (RFP) marker with at least some of the seeds containing a genetic element of interest of the bulk sample, evaluating at least some of the seeds of the bulk sample for the presence or absence of the RFP marker using an evaluating device, and sorting the seeds containing a genetic element of interest based on the presence or absence of the RFP marker.

In some embodiments, the RFP marker is discernable when excited by a certain energy having a wavelength ranging from substantially about 500 nm to substantially about 580 nm. In some such embodiments, the certain energy may have a peak at substantially about 550 nm. In other embodiments, the evaluating step comprises exciting the seeds containing a genetic element of interest with the certain energy; and detecting an emission resulting at least in part from the exciting step. In some such embodiments, the resulting emission may have a wavelength ranging from substantially about 500 nm to substantially about 600 nm. Furthermore, the emission may have a peak at substantially about 580 nm. In some embodiments, the evaluating device may further comprise at least one filter disposed substantially between the image sensing device and the seeds containing a genetic element of interest. The filter may be configured for passing the emission from the red fluorescent protein marker to the image sensing device.

Some embodiments may further comprise associating a plurality of supplemental markers with at least some of the seeds containing a corresponding plurality of additional genetic elements of interest of the bulk sample. Such embodiments may further comprise steps for evaluating at least one of the seeds of the bulk sample for the presence or absence of the plurality of supplemental markers using the evaluating device, and sorting the seeds containing the plurality of additional genetic elements of interest based on the presence or absence of the a plurality of supplemental markers. In such embodiments, the supplemental markers may include, but are not limited to: yellow fluorescent proteins; yellow/orange fluorescent proteins; orange fluorescent proteins; orange/red fluorescent proteins; red/orange fluorescent proteins; red fluorescent proteins; cyan fluorescent proteins; and combinations of such supplemental markers.

In some embodiments, the evaluating device may be a seed color sorter. In other embodiments, the image sensing device may be a charge-coupled device (CCD device) or a complementary metal oxide semiconductor (CMOS) device. In other embodiments, the evaluating step comprises evaluating seeds for the presence of a RFP marker using at least one image sensing device configured to differentiate between a range of normal seed emissions and the discernable RFP marker. In other embodiments, the sorting step may comprise dispensing the sorted individual seeds into at least one container, the container including only seeds having the RFP marker present or only seeds in which the RFP marker is absent.

Other embodiments further comprise steps for singulating individual seeds from the bulk sample using a singulating device. In some embodiments, the singulating step comprises singulating seeds using a plurality of elongate hollow structures operatively connected to a vacuum source. In other embodiments, the singulating step comprises receiving the bulk sample in a hopper and vibrating the hopper so as to propel individual seeds along an inclined spiral ramp and through a gap configured to permit the passage of one seed at a time. In other embodiments, the singulating step comprises receiving the bulk sample in a hopper, feeding seeds from the hopper to a rotatable disk, and rotating the rotatable disk so as to distribute the seeds to a periphery of the rotatable disk by application of centrifugal force. In other embodiments, the singulating step comprises receiving the bulk sample in a hopper, vibrating the bulk sample such that seeds tend to move towards an opening in the hopper, distributing seeds from the opening in the hopper to a sloped device that includes at least one groove such that a line of individual seeds is formed in the groove, and depositing individual seeds by gravity force from the sloped device onto a conveying device.

Thus the various embodiments of distinguishing seeds containing a genetic element of interest of the present invention provide many advantages that may include, but are not limited to: providing a method and computer program product capable of permitting a bulk sample of seeds to be sorted based on the presence or absence of a marker or multiple RFP markers, associated with a selected genotype, or multiple selected genotypes. The present invention provides a level of convenience, speed, accuracy, and environmental safety that is not available using conventional techniques. Additionally, the present invention provides additional processing of the sorted seeds, including dispensing the sorted seeds into containers.

These advantages, and others that will be evident to those skilled in the art, are provided in the method and computer program product of the present invention.

BRIEF DESCRIPTION OF THE DRAWINGS

Figure 1:
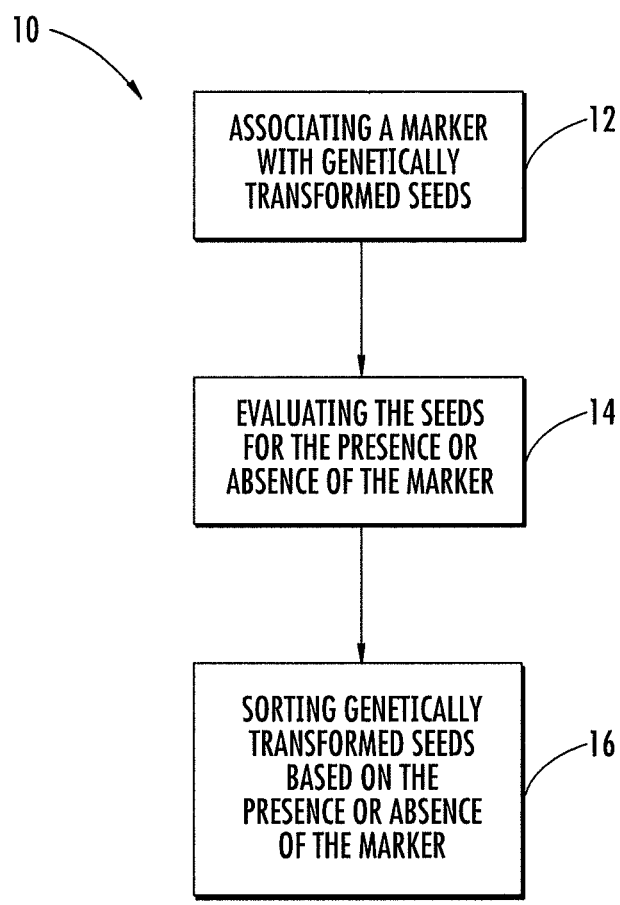
Figure 2:
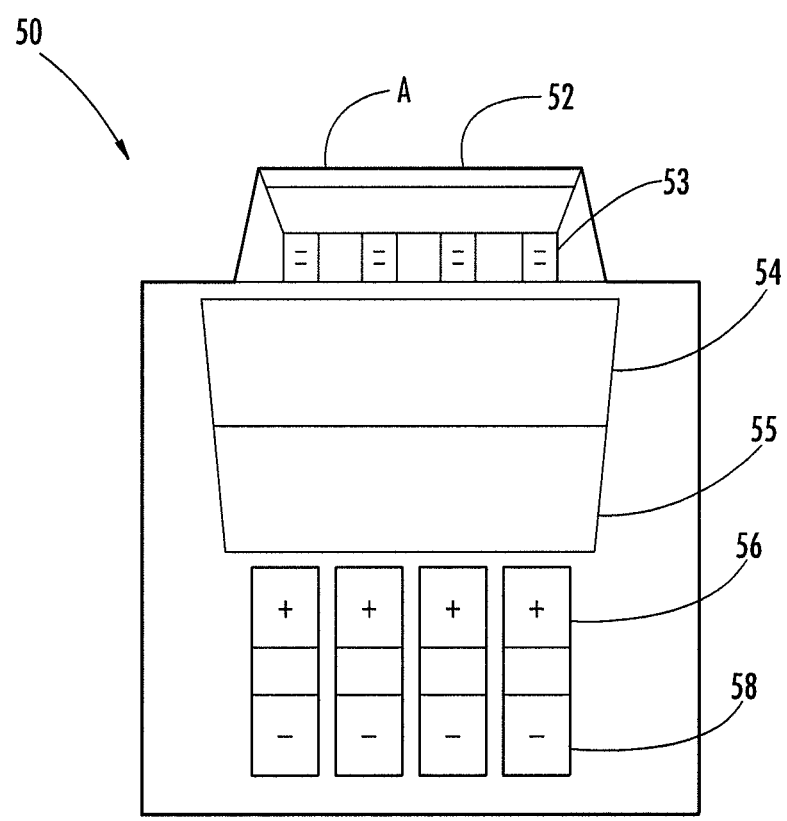
Figure 3:
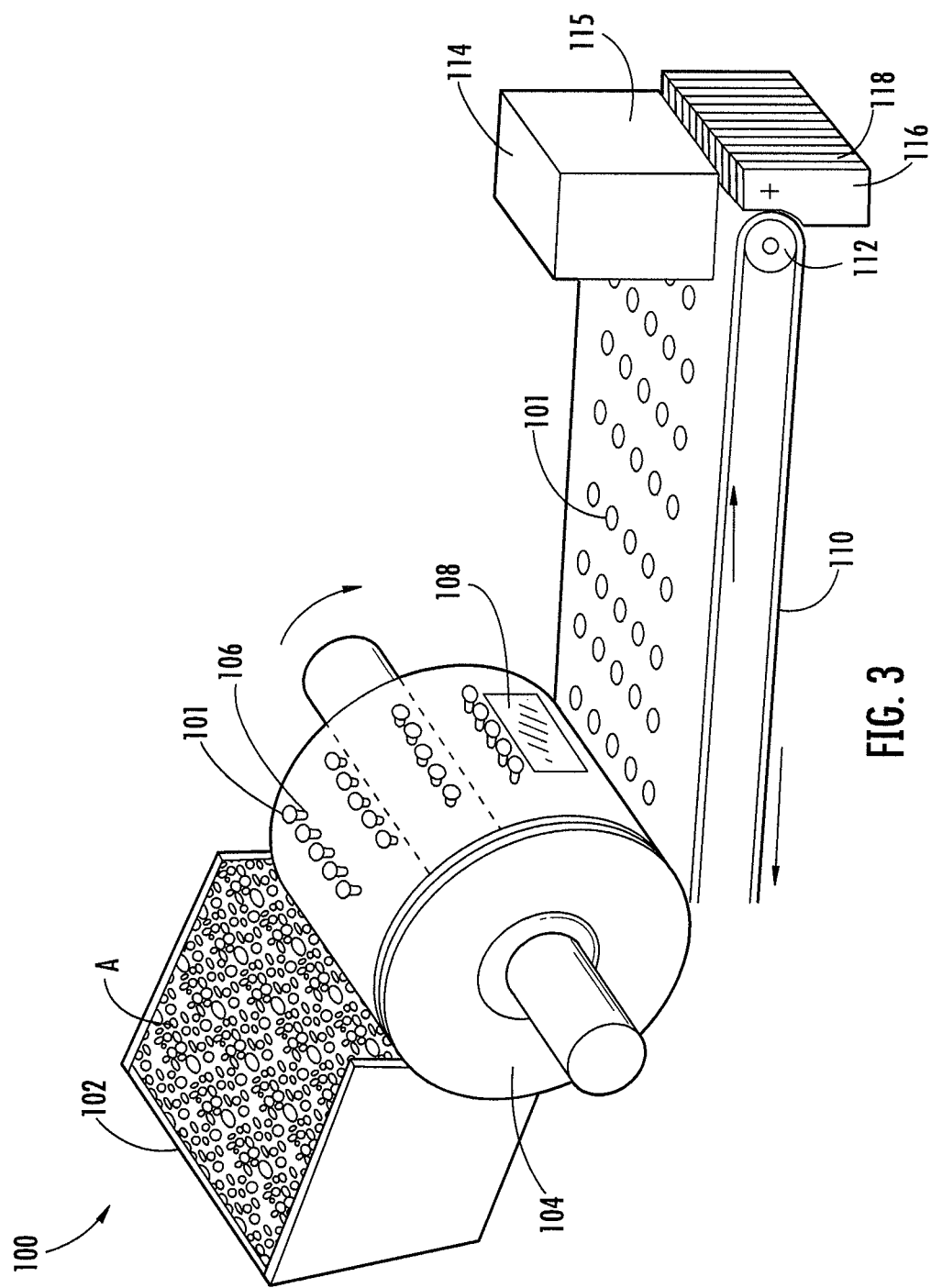
Figure 4:
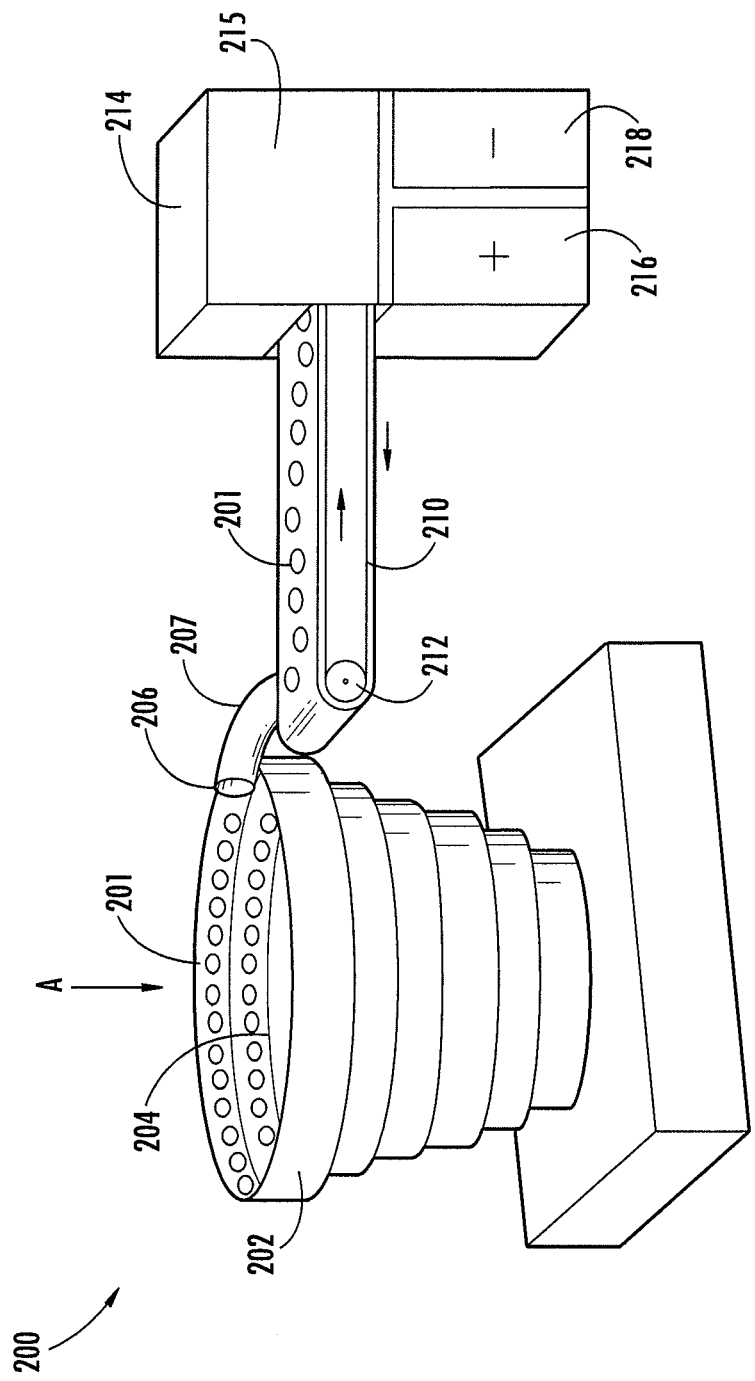
Figure 5:
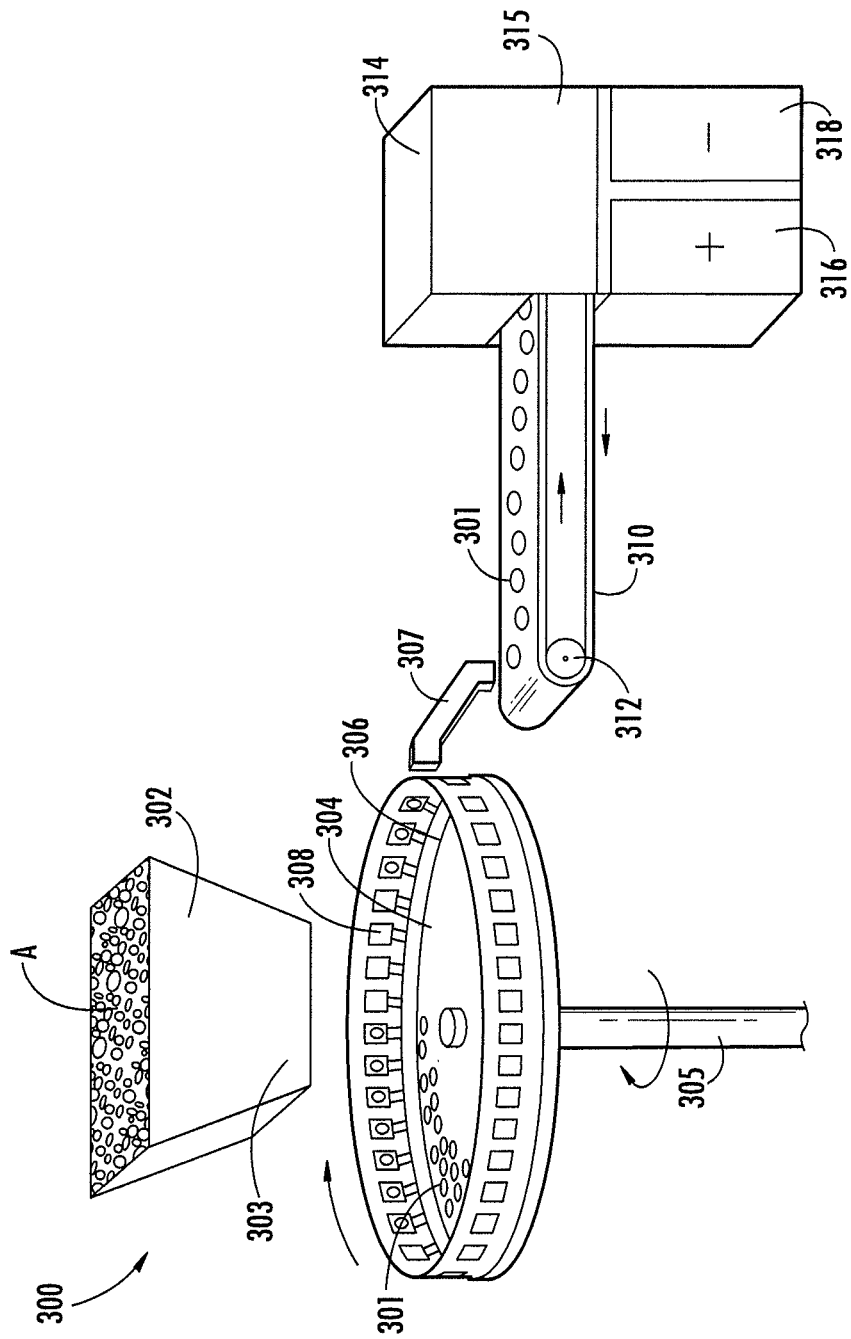
Figure 6:
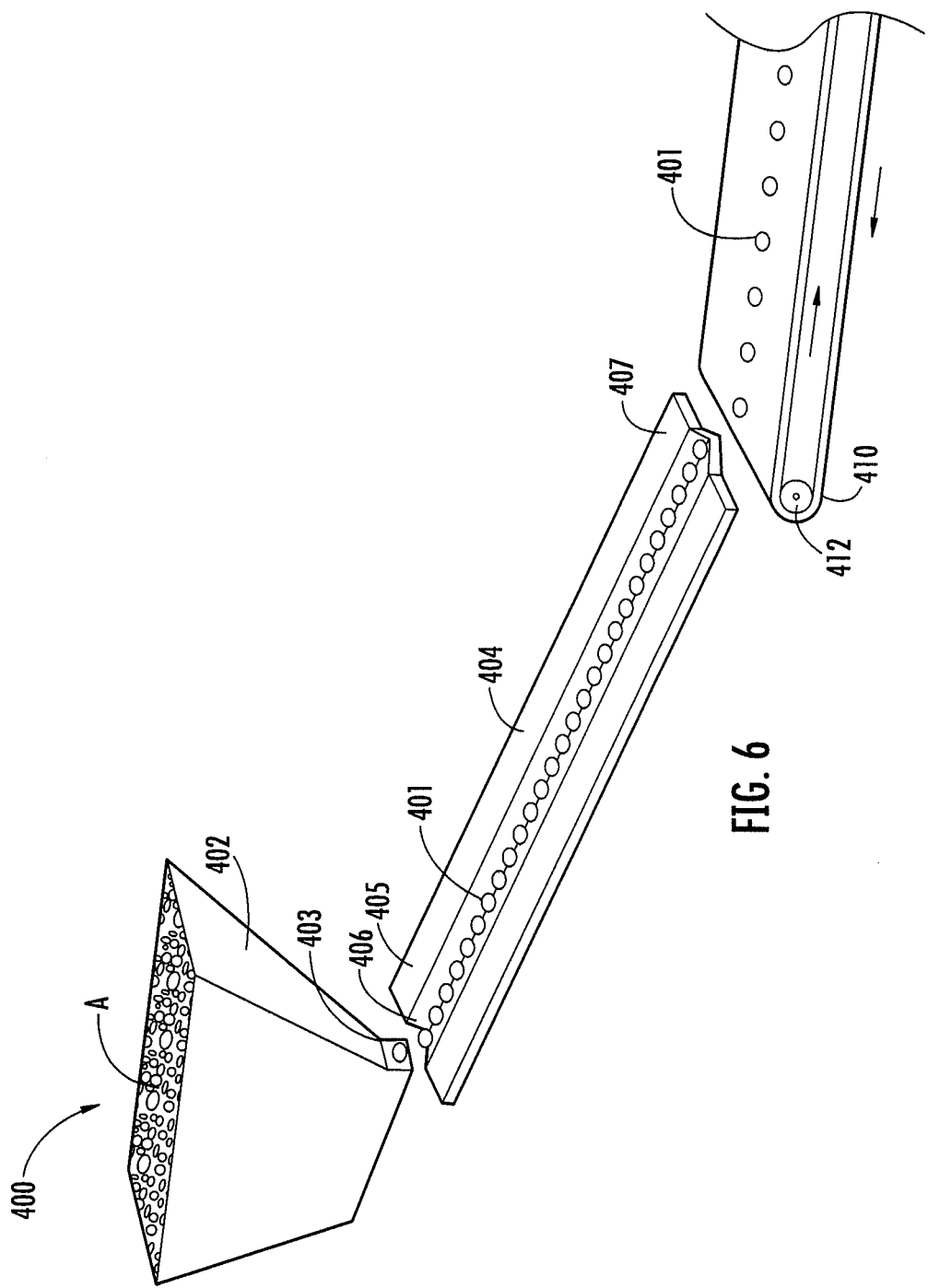
Figure 7:
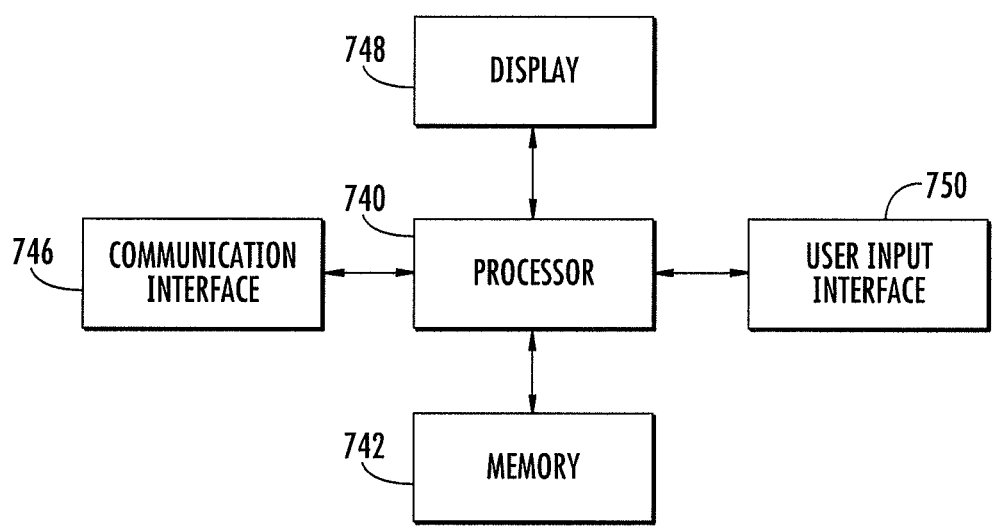
Figure 8:
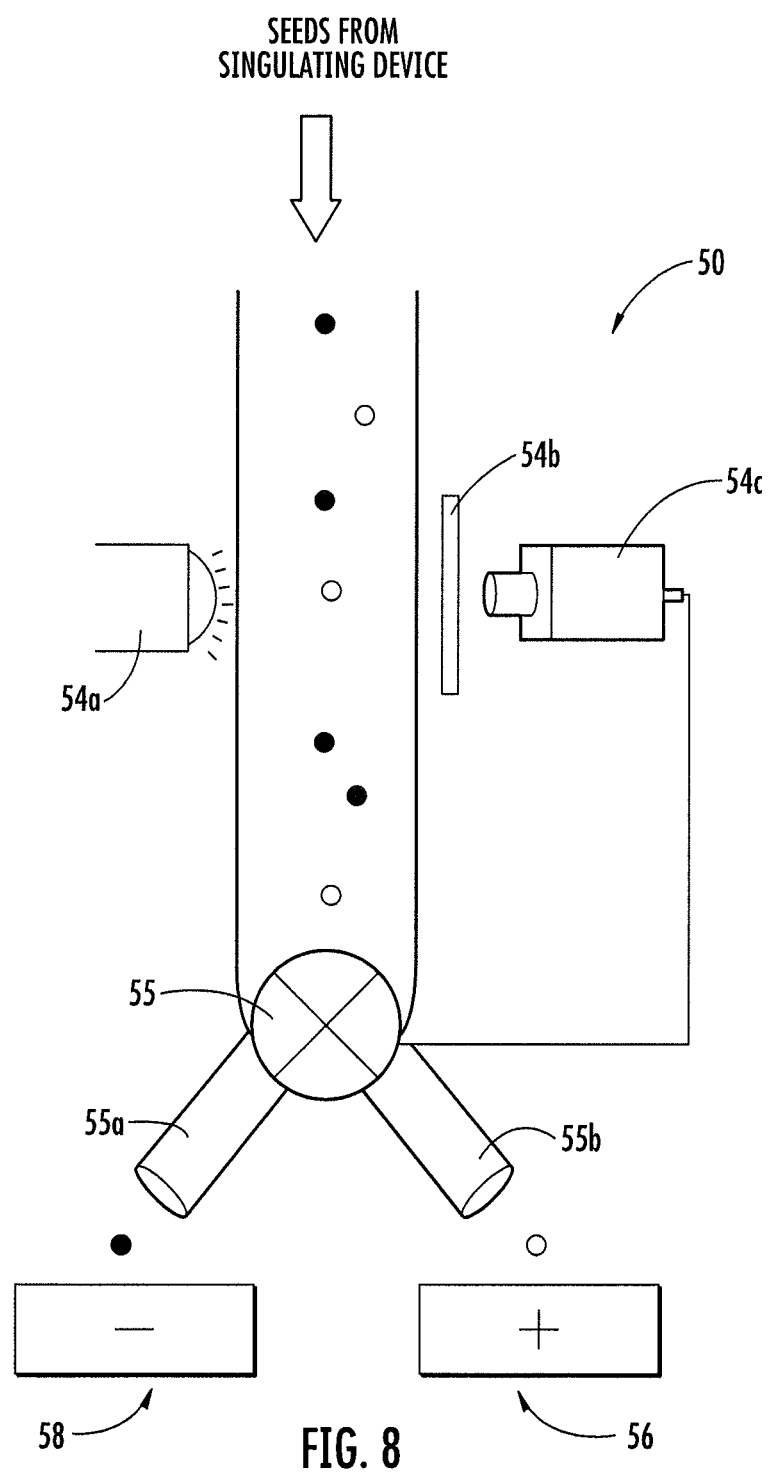
Figure 9:
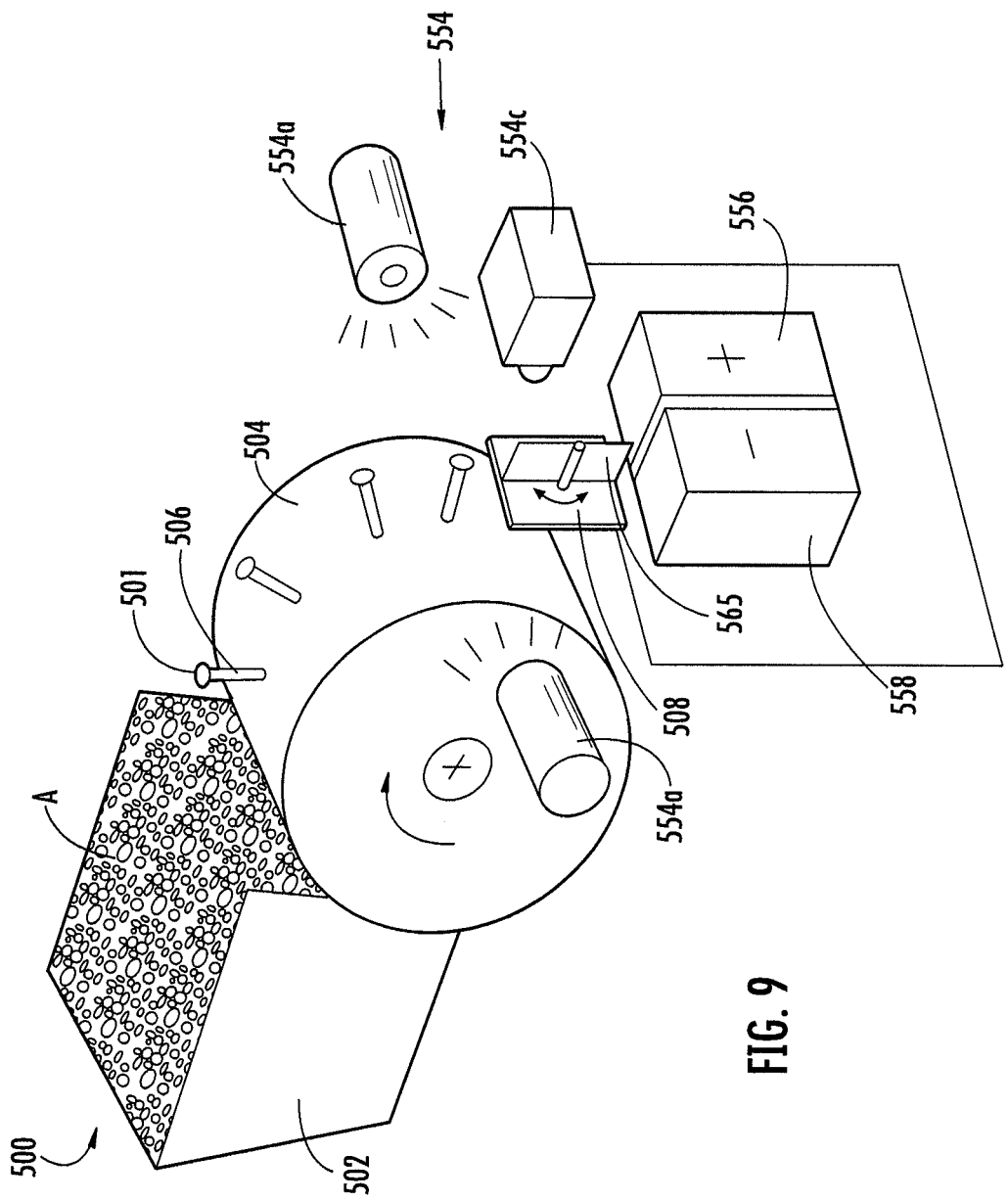
Figure 10:
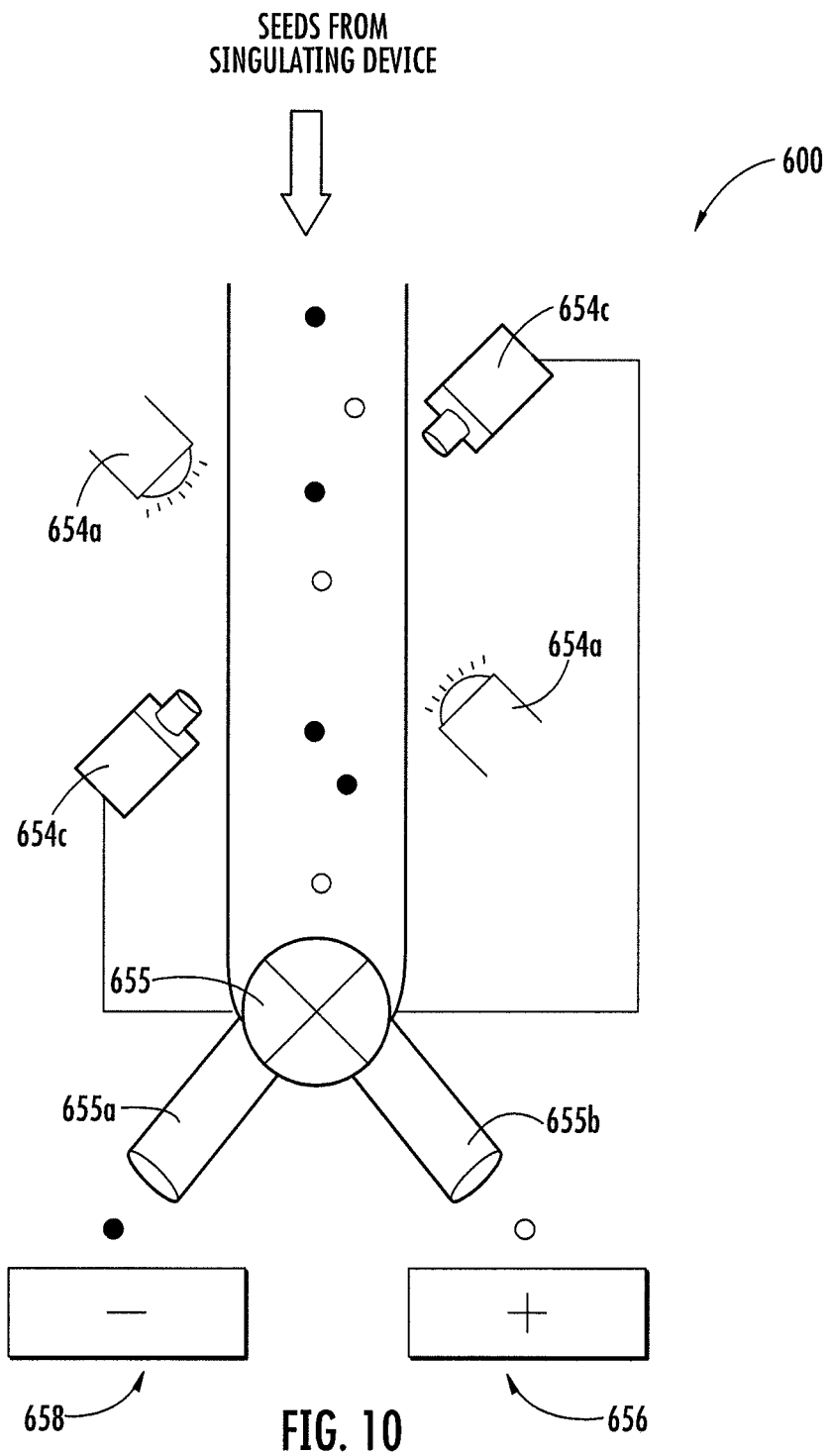

Having thus described the invention in general terms, reference will now be made to the accompanying drawings, which are not necessarily drawn to scale, and wherein:

FIG. 1 shows a flow chart of a method, according to one embodiment of the present invention, including steps for associating a marker with seeds containing a genetic element of interest, evaluating the seeds for the presence of the marker, and sorting the seeds based on the presence or absence of the marker;

FIG. 2 shows a non-limiting schematic of a seed sorter device used to distinguish seeds containing a genetic element of interest in accordance with one embodiment of the present invention;

FIG. 3 shows a non-limiting schematic of a system incorporating a vacuum drum singulating device for singulating seeds prior to evaluating and separating seeds based on the presence of a marker in accordance with one embodiment of the present invention;

FIG. 4 shows a non-limiting schematic of a system incorporating a hopper having an inclined ramp for singulating seeds prior to evaluating and separating seeds based on the presence of a marker in accordance with one embodiment of the present invention;

FIG. 5 shows a non-limiting schematic of a system incorporating a rotatable disk for singulating seeds prior to evaluating and separating seeds based on the presence of a marker in accordance with one embodiment of the present invention; and FIG. 6 shows a non-limiting schematic of a system incorporating an inclined ramp having a groove feature for singulating seeds prior to evaluating and separating seeds based on the presence of a marker in accordance with one embodiment of the present invention;

FIG. 7 shows a non-limiting block diagram of an exemplary electronic device configured to distinguish genetically transferred seeds from a bulk sample of exemplary embodiments of the present invention;

FIG. 8 shows a non-limiting schematic of a seed sorter device used to distinguish seeds containing a genetic element of interest in accordance with one embodiment of the present invention;

FIG. 9 shows a non-limiting schematic of a system incorporating a vacuum drum singulating device and a pair of illuminating devices in accordance with one embodiment of the present invention; and FIG. 10 shows a non-limiting schematic of a seed sorter device incorporating a pair of illuminating devices and a pair of evaluating devices used to distinguish seeds containing a genetic element of interest in accordance with one embodiment of the present invention.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Under current methods, it is difficult to distinguish, prior to germination, seeds that contain a genetic element of interest from seeds that do not contain such elements. To address this concern, various embodiments of the present invention provide a method and computer program product that sorts seeds based at least in part on the relationship between a discernable marker and one or more seeds containing a genetic element of interest. For the purposes of the current specification and the appended claims, the term "discernable" refers to an ability to recognize a marker when excited by certain energy. In various embodiments, this may include the visible portion of the electromagnetic spectrum, as well as Ultraviolet and Infrared spectrums.

FIG. 1 shows a flowchart illustrating a method 10 for distinguishing seeds containing a genetic element of interest from a bulk sample. In step 12, a marker is associated with at least a portion of seeds containing a genetic element of interest from the bulk sample. In various embodiments, associating a marker with at least a portion of seeds containing a genetic element of interest may comprise a variety of techniques used to mark a desired genotype. In an exemplary embodiment, associating a marker with at least a portion of seeds containing a genetic element of interest comprises attaching DNA sequences that code for red fluorescent protein (RFP) to a desired trait DNA sequence that is inserted into a seed or a group of seeds. It should be noted that although the exemplary embodiment described below associates an RFP marker with a desired trait, in other embodiments multiple fluorescent protein (FP) markers may be associated with a desired trait DNA sequence or multiple desired trait DNA sequences in the same seed. Such additional FP markers may include, but are not limited to: yellow; yellow/orange; orange; orange/red, red/orange; red (including the RFP described herein); and cyan. In other embodiments, the marker may comprise phenotypic markers such as β-galactosidase and fluorescent proteins such as cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) Proc. *Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. In other embodiments, the marker may also comprise a selectable marker gene for the selection of transformed cells.

The above lists are not meant to be limiting. Any desired trait and marker may be used in the present invention.

In various embodiments, the desired trait DNA sequence may correspond substantially to any trait desired to be inserted into a plant genome.

In one exemplary embodiment, the marker associated with at least a portion of seeds containing a genetic element of interest from the bulk sample in step 12 may comprise a RFP marker such as the DsRed and/or DsRed2 RFP markers from the Living Colors™ line of novel fluorescent proteins (NFP)

commercially available from Clontech Laboratories, Inc. of Mountain View, Calif. The use of RFP as the marker may provide several advantages over other fluorescent protein markers (such as green fluorescent protein (GFP)). For example, unlike GFP, RFP excitation and emission wavelengths are closer to a center of the visible range of the electromagnetic spectrum. Therefore, RFP-expressing seed may be visible to the eye (and unassisted and/or unmodified cameras or other sensor devices) in 'normal' ambient white light. Thus, seed sorting (step 16, for example) may be accomplished in such embodiments without the need for specialized UV light sources and/or detectors. Furthermore, many commercially available and industry-proven high-speed sorting devices operate most effectively in the visible range of the electromagnetic spectrum. Again as above, since RFP excitation and emission wavelengths are predominantly centered in the visible range of the electromagnetic spectrum, sorting (step 16) may be accomplished using existing and readily-available equipment as an add-on to the current use for more standard quality sorting procedures. Furthermore, RFP (and specifically DsRed2) markers are optimized for minimal protein aggregation, such that the marker may avoid issues with in vivo protein aggregation that may affect product performance (i.e. seed viability and/or yield) as well as produce potentially negative environmental effects that run counter to principles of product stewardship.

Step 12 may comprise, in some embodiments, associating the RFP marker with one or more desired trait DNA sequences that may be inserted into a seed or a group of seeds. For example, genetically engineered plants and/or seeds may contain beneficial traits of interest such as one or more genes expressing peptides with pesticidal and/or insecticidal activity, such as Bt toxic proteins (described in, for example, U.S. Pat. Nos. 5,277,905; 5,366,892; 5,747,450; 5,723,756; 5,859, 336; 5,593,881; 5,625,136; 5,689,052; 5,691,308; 5,188,960; 6,180,774; 6,023,013; 6,218,188; 6,342,660; 6,114,608; and 7,030,295; US Publication Nos: US20040199939 and US20060085870; WO2004086868; and Geiser et al. (1986) *Gene* 48:109) and Bt crystal proteins of the Cry34 and Cry35 classes (see, e.g., Schnepf et al. (2005) *Appl. Environ. Microbiol.* 71:1765-1774), and vegetative insecticidal proteins (for example, members of the VIP1, VIP2, or VIP3 classes, see, for example, U.S. Pat. Nos. 5,849,870; 5,877,012; 5,889,174; 5,990,383; 6,107,279; 6,137,033; 6,291,156; 6,429,360; as well as U.S. Pat. App. Publication Nos: US20050210545; US20040133942; and US20020078473), lectins (Van Damme et al. (1994) *Plant Mol. Biol.* 24:825, pentin (described in U.S. Pat. No. 5,981,722), lipases (lipid acyl hydrolases, see, e.g., those disclosed in U.S. Pat. Nos. 6,657,046 and 5,743,477), cholesterol oxidases from *Streptomyces*, and pesticidal proteins derived from *Xenorhabdus* and *Photorhabdus* bacteria species, *Bacillus laterosporus* species, and *Bacillus sphaericus* species, and the like. Also contemplated is the use of chimeric (hybrid) toxins (see, e.g., Bosch et al. (1994) *Bio/Technology* 12:915-918).

Genetically engineered plants and/or seeds thereof can also contain one or more genes with a variety of desired trait combinations including, but not limited to, traits desirable for animal feed such as high oil genes (e.g., U.S. Pat. No. 6,232, 529); balanced amino acids (e.g., hordothionins (U.S. Pat. Nos. 5,990,389; 5,885,801; 5,885,802; and 5,703,049); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. Pat. No. 6,858,778); and thioredoxins (U.S. Pat. No. 7,009,087)). Such plants can also contain one or more genes resulting in traits desirable for disease resistance (e.g., fumonisin detoxification genes (U.S. Pat. No. 5,792,931); avirulence and disease resistance genes (Jones et al. (1994) *Science* 266:789; Martin et al. (1993) *Science* 262: 1432; Mindrinos et al. (1994) *Cell* 78:1089).

Genetically modified plants may further contain one or more genes encoding one or more forms of herbicide resistance, for example, to glyphosate-N-(phosphonomethyl) glycine (including the isopropylamine salt form of such herbicide). Exemplary herbicide resistance genes include glyphosate N-acetyltransferase (GAT) and 5-enolpyruvylshikimate-3-phosphate synthase (EPSPS), including those disclosed in U.S. Pat. Application Publication Nos: US20040082770, also WO02/36782 and WO03/092360). Herbicide resistance genes generally code for a modified target protein insensitive to the herbicide or for an enzyme that degrades or detoxifies the herbicide in the plant before it can act. See, e.g., DeBlock et al. (1987) *EMBO J.* 6:2513; DeBlock et al. (1989) *Plant Physiol.* 91:691; Fromm et al. (1990) *BioTechnology* 8:833; Gordon-Kamm et al. (1990) *Plant Cell* 2:603; and Frisch et al. (1995) *Plant Mol. Biol.* 27:405-9. For example, resistance to glyphosate or sulfonylurea herbicides has been obtained using genes coding for the mutant target enzymes, EPSPS and acetolactate synthase (ALS). Resistance to glufosinate ammonium, bromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides. Also contemplated are inhibitors of glutamine synthase such as phosphinothricin or basta (e.g., bar gene).

Transgenic plants and/or seeds may also contain one or more genes resulting in traits desirable for processing or process products such as modified oils (e.g., fatty acid desaturase genes (U.S. Pat. Nos. 5,952,544; 6,372,965)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847)). Such plants could also contain one or more genes providing agronomic traits such as male sterility (e.g., see U.S. Pat. No. 5,583,210), stalk strength, flowering time, or transformation technology traits such as cell cycle regulation or gene targeting (e.g., WO 99/61619, U.S. Pat. Nos. 6,518,487 and 6,187, 994).

In step 14, the seeds from the bulk sample are evaluated for the presence or absence of the RFP marker. In various embodiments, this step 14 may comprise visually determining whether the RFP marker is present or absent in a seed or a group of seeds. In an exemplary embodiment, step 14 comprises exciting seeds from the bulk sample with a certain energy and then determining whether the RFP marker is present. The certain energy used to illuminate the seeds (and/or excite the RFP markers that may be present therein) may have a wavelength substantially within the visible electromagnetic spectrum (i.e. a wavelength ranging from substantially about 500 nm to substantially about 580 nm). In some embodiments the certain energy emitted as part of step 14 may exhibit a peak at substantially about 550 nm. In some embodiments, step 14 may further comprise detecting an emission resulting at least in part from the exciting step, wherein the emission may have a wavelength ranging from substantially about 500 nm to substantially about 600 nm. In some embodiments, the emission resulting from step 14 may exhibit a peak at substantially about 580 nm.

Various evaluating devices may be used for the determination performed in step 14. For example, evaluating devices may include, but are not limited to, commercially available optical seed sorters, such as a ScanMaster II seed sorter manufactured by Satake-USA. Although in normal usage, seed sorters may be used to evaluate and sort out contaminants such as rocks, glass, soil, damaged food items, mold, and other foreign material from a bulk sample of food items, an exemplary embodiment of the present invention modifies a seed sorter to evaluate and sort seeds expressing a fluorescent protein that is attached to a desired trait DNA sequence that has been inserted into a seed or a group of seeds in the bulk sample.

As shown generally in FIG. 8, such optical seed sorters may include a specialized vision system 54 which, in some embodiments, may comprise: (1) an illuminating device 54a (such as a bulb, for example) that emits electromagnetic energy at a particular frequency (characterizing the "certain energy" described herein) chosen to illuminate and thereby "excite" the RFP marker, and (2) a filter 54b used that may be used to filter the energy emitted (i.e. "the emission") from the RFP-tagged seeds so that a camera 54c (or other image sensing device) of the vision system may discern seeds expressing the RFP marker.

To accomplish this task, in one method embodiment of the present invention, the evaluating step 14 may comprise evaluating seeds for the presence of the RFP marker using at least one image sensing device 54c configured to differentiate between a range of normal seed emissions and an emission from the RFP marker. As described herein, such an image sensing device 54c may comprise a component of a commercially available color sorter device. Furthermore, in some embodiments, the image sensing device 54c may comprise a CCD device and/or a CMOS device configured for detecting the emission from RFP-tagged transgenic and/or otherwise genetically-modified seeds.

As shown in FIG. 8, in some embodiments, the evaluating device employed as part of the evaluating step 14 may further comprise at least one filter 54b disposed substantially between an image sensing device 54c (such as a CCD) and the seeds containing a genetic element of interest. The at least one filter 54b may be configured for passing the emission from the red fluorescent protein marker to the image sensing device 54c. For example, in some embodiments, the filter 54b may comprise a band-pass filter configured for passing electromagnetic energy having a wavelength that is substantially equivalent to the targeted emission wavelength (i.e. the emission wavelength of energy emitted from an illuminated and subsequently excited RFP marker (such as DsRed2, for example). The emission may then be detected by the image sensing device 54c that may be further configured for translating the emission into substantially "white" light. Thus, the image sensing device may assign substantially binary values to each seed based on the presence or absence of the RFP marker wherein seeds containing a genetic element of interest (tagged with the relatively "bright" RFP marker) are marked "positive" (and thereby deflected and/or other wise directed into one or more "+" containers 56. Seeds that do not contain a genetic element of interest, or other particulate debris (which may be translated into a "dark" or "negative" result) may be dropped and/or otherwise directed into one or more "−" containers 58. As shown in FIG. 8, the image sensing device 54c (or other component of a vision system 54 may be in communication with a sorting device 55 (which may comprise, for example, a valve device and/or compressed air jet device) configured for directing the "positive" (i.e. seeds containing a genetic element of interest (which the image sensing device 54c may detect as "white" or "bright" seeds)) into one or more "+" containers 56 in response to a binary positive or "1" signal received from the image sensing device 54c or other processing component of the vision system 54. The sorting device 55 may also be configured for directing the "negative" (i.e. seeds that do not contain a genetic element of interest or particulate debris (which the image sensing device 54c may detect as "dark" seeds)) into one or more "−" containers 58 in response to a binary negative or "0" signal received from the image sensing device 54c or other processing component of the vision system 54. While the system 50 shown in FIG. 8 is shown oriented in a substantially vertical orientation (such that individual seeds pass through the vision system components 54a, 54b, 54c in response to gravity forces) in should be understood that the system 50 may also be oriented substantially horizontally and may comprise one or more pressurized pneumatic tubes and/or conveyance pathways configured for directing individual seeds from a sample past the various vision system components 54a, 54b, 54c and subsequently to a sorting device 55 that may be configured for transferring the seeds containing a genetic element of interest into corresponding "+" containers 56 and for transferring the seeds not containing the genetic element of interest into corresponding "−" containers 58 in response to signals received from one or more vision system 54 components and/or controllers.

As described herein, some embodiments of the present invention may utilize a plurality of supplemental markers (such as a variety of fluorescent protein markers) to highlight the presence and/or absence of a corresponding plurality of additional genetic elements of interest in the seeds of the bulk sample. For example, as described herein, various embodiments of the present invention may utilize supplemental markers that may include, but are not limited to: yellow fluorescent proteins; yellow/orange fluorescent proteins; orange fluorescent proteins; orange/red fluorescent proteins; red/orange fluorescent proteins; red fluorescent proteins; cyan fluorescent proteins; and combinations of such supplemental markers. Referring generally to FIG. 1, such embodiments may comprise step 12 for associating one or more of a plurality of supplemental markers with at least some of the seeds containing a corresponding plurality of additional genetic elements of interest of the bulk sample. Some such embodiments may further comprise step 14 for evaluating at least one of the seeds of the bulk sample for the presence or absence of the plurality of supplemental markers using the evaluating device and subsequently, step 16 for sorting the seeds containing the plurality of additional genetic elements of interest based on the presence or absence of the a plurality of supplemental markers.

In some such embodiments, the evaluating step 14 may comprise evaluating seeds for the presence of at least one of the plurality of supplemental markers using at least one image sensing device 54 configured to differentiate between a range of normal seed emissions and at least one emission from one or more of the plurality of supplemental markers. As described herein, in some embodiments, the image sensing device 54 may comprise a CCD device or a CMOS device. As shown generally in FIG. 8, the evaluating device used to perform the evaluating step 14 may comprise a specialized vision system 54 which, in some embodiments, may comprise: (1) an illuminating device 54a (such as a bulb, for example) that emits electromagnetic energy at a particular frequency (characterizing the "certain energy" described herein) chosen to illuminate and thereby "excite" the RFP marker, and (2) a filter 54b used that may be used to filter the energy emitted (i.e. "the emission") from the RFP-tagged seeds so that a camera 54c (or other image sensing device) of the vision system may discern seeds expressing the RFP marker. In some embodiments wherein a plurality of supplemental markers (which may each exhibit a characteristic emission frequency, for example) are used to "tag" a corresponding plurality of additional genetic elements that may be present in the seeds, the filter 54b may comprise at least one tunable filter disposed substantially between the image sensing device 54c and the seeds containing a genetic element of interest. The at least one tunable filter 54b may be configured for selectively passing the at least one emission from one or more of the plurality of supplemental markers to the image sensing device 54c. In such embodiments, the tunable filter 54c may allow the evaluating device to selectively sort for a plurality of different genetic elements of interest that may be present in the seed sample. In one exemplary embodiment, the filter device 54c may comprise a VariSpec™ Liquid Crystal Tunable Filter (LCTF) commercially available from CRI, Inc. of Woburn, Mass. In some such embodiments, the filter 54b may be "tuned" to sequentially sense and sort seeds based on "positive" emissions from seeds having one particular genetic element of interest (that corresponds, for example, to one of a plurality of supplemental markers and/or the base RFP) during a sequence of passes through the evaluating device 54.

FIG. 2 shows a schematic representation of another exemplary system 50 that may be used to distinguish seeds containing a genetic element of interest from a bulk sample of seeds in accordance with one exemplary embodiment. In the exemplary embodiment, the system 50 is a modified commercially available seed sorter. A bulk sample A of seeds, at least some of which have been genetically transformed by inserting a desired trait DNA sequence with an attached DNA sequence that codes for fluorescent proteins, are loaded into a hopper 52. The hopper 52 is configured to funnel the bulk sample A of seeds into separate chutes 53 that are sized to accommodate a particular volume for processing by a vision system 54. The seeds from each chute 53 fall by force of gravity past the vision system 54. In the exemplary embodiment, the vision system 54 comprises an illuminating device, at least one sensing device, and a controller configured to control the illuminating and sensing devices.

In the exemplary embodiment, the illuminating device comprises a light source that uses a bulb configured to emit electromagnetic radiation at a wavelength spectrum that illuminates the RFP marker. In other embodiments, the light source may be any light source that permits the image sensing device to discern the RFP marker. As such, in various embodiments the light source and the marker may be paired so as to increase the ability of the vision system to discern the presence of the marker. The exemplary embodiment includes multiple CCD cameras with filters (i.e. red band-pass filters) configured to enhance the illumination and to aid in discerning the presence of the RFP marker. Although other embodiments may use fewer cameras, the exemplary embodiment allows seeds falling past the vision system 54 to be viewed from the front and back. In other embodiments, any vision system 54 configured to discern the presence of a RFP marker may be used, including, but not limited to, CCD devices, CMOS devices and other vision sensors.

Step 16 of FIG. 1 relates to sorting the seeds containing a genetic element of interest based on the presence or absence of the marker. The sorting function is carried out by a sorting device. In the exemplary embodiment shown in FIG. 2, the sorting device 55 comprises a number of individual pneumatic ejectors that emit a controlled blast of air (such as an "air knife" for example) configured for sorting seeds that exhibit the RFP marker as the seeds pass through the sorting device. Seeds exhibiting the RFP marker are sorted into containers 56, identified in the figure with a "+" symbol. Seeds that do not contain the marker fall into containers 58, identified in the figure with a "−" symbol. Although not shown in the figure, in other embodiments the seeds contained in the "−" container 58 may be re-routed through the hopper 52 so that these seeds make a successive pass through the system 50. In such a manner any seeds that were not identified as exhibiting the marker may be identified in one or more successive passes through the system 50.

The above described method allows the processing of a large quantity of seeds, a portion of which include a marker that is associated with a genetically transformed seed including a desired trait. However in other embodiments, a bulk sample may include various seeds having different markers associated with different desired traits, or seeds that include more than one marker associated with different desired traits. Although the exemplary embodiment described above may accommodate these situations, in other instances it may be advantageous to evaluate seeds on a seed-by-seed basis. As a result, in various embodiments, the present invention contemplates singulating seeds from a bulk sample prior to evaluating the seeds for the presence or absence of a marker or a group of markers associated with a desired trait or group of traits.

FIG. 3 shows a system 100 employing the above method in accordance with one embodiment of the present invention. The system 100 shown in the figure includes an exemplary embodiment of a singulating device comprising a plurality of elongate hollow structures operatively connected to a vacuum source used to singulate seeds from a bulk sample. Specifically, the system 100 of the exemplary embodiment includes a hopper 102 into which a bulk sample A of seeds may be placed. A rotating drum 104 is positioned adjacent the hopper 102. The rotating drum 104 includes a plurality of elongate hollow structures 106 that extend into a substantially hollow interior of the drum 104, which is connected to a vacuum source (not shown). The vacuum source creates a zone of negative pressure within the interior of the drum 104, and as a result, distal ends of the elongate hollow structures 106 create discrete areas of negative pressure. As shown in the figure, the drum 104 rotates adjacent an open end of the hopper 102. The hopper 102 is configured such that seeds are urged toward the open end and adjacent the rotating drum 104. The drum 104 rotates in the direction shown such that the elongate hollow structures 106 pass through a portion of the seeds of the bulk sample A adjacent the drum 104. As the elongate hollow structures 106 rotate through the bulk sample A, the discrete areas of negative pressure located at the distal ends of the elongate hollow structures 106 attract individual seeds 101. The size of the distal ends of each of the elongate hollow structures 106 is configured such the discrete area of negative pressure at the distal end of each of the hollow structures 106 attracts a single seed 101. As shown in the figure, as the elongate hollow structures 106 rotate through the open end of the hopper 102, individual seeds 101 attach to the distal ends of the elongate hollow structures 106. As the drum 104 continues to rotate in the direction shown, the seeds 101 travel toward a conveyor belt 110. Rotating driving members 112 drive the conveyor belt 110 in the direction shown. In various embodiments, the speed of the driving members 112 may be adjusted to optimize downstream evaluating and sorting of the seeds 101.

At a position adjacent the conveyor belt 110, a deflector plate 108 (or alternatively, in some embodiments, a compressed air source configured for detaching individual seeds from the elongate hollow structures 106) deflects the seeds 101 from the distal ends of the elongate hollow structures 106 and onto the conveyor belt 110. In the exemplary embodiment, the deflector plate 108 contacts between the distal ends of the elongate hollow structures 106 and the seeds 101 carried by them so that the area of negative pressure is temporarily blocked, effectively releasing the seeds 101 from the distal ends of the elongate hollow structures 106. Thus, the seeds 101 are singulated along the conveyor belt 110. In various embodiments, the rotating drum 104 may have a single radial pattern of elongate hollow structures 106, or, as shown in the figure, it may have a series of elongate hollow structures 106 arranged in a radial pattern.

A vision system 114 and sorting system 115 are shown downstream from the rotating drum. As noted above, the vision system 114 comprises an illuminating device, at least one sensing device, and a controller configured to control the illuminating and sensing devices. In the exemplary embodiment, the illuminating device comprises a light source that uses a bulb configured to emit electromagnetic radiation at a wavelength spectrum matched to illuminate the fluorescent protein marker. The exemplary embodiment includes multiple CCD cameras and filters configured to enhance the illumination and to aid in discerning the presence of the marker. The seeds 101 are sorted by the sorting system into "+" containers 116 and "−" containers 118. In the exemplary embodiment, a series of mechanical deflectors and/or valves (see element 55, FIG. 8, for example) are used to sort the pattern of singulated seeds based on the presence or absence of the marker. The seeds containing the marker are sorted into the "+" containers 116; the seeds that do not contain the marker are sorted into the "−" containers 118. Although not shown in the figure, in other embodiments the seeds contained in the "−" container 118 may be re-routed through the hopper 102 so that these seeds make a successive pass through the system 100. In such a manner any seeds that were not identified as exhibiting the marker may be identified in one or more successive passes through the system 100.

FIG. 4 shows another exemplary embodiment of a singulating, evaluating, and sorting system 200 employing a method in accordance with one embodiment of the present invention. In the exemplary embodiment, a vibratory stepped bowl 202 is configured to singulate seeds from a bulk sample A and pass the singulated seeds 201 through an exit aperture 206 which may be located, for example, near an upper periphery of the stepped bowl 202 of the system 200. For example, in some embodiments, the system may include a commercially-available seed counter (such as the Seedburo 801 Count-A-Pak™ vibratory counter device manufactured by Seedburo Equipment Company in Chicago, Ill.). In such embodiments, the seeds 201 of the bulk sample A may be loaded into the stepped bowl 202 of the system 200 such that as the stepped bowl 202 is vibrated, the seeds 201 may be lined up in single file along a periphery of the tracks 204 defined on the steps of the stepped bowl 202 and advanced toward the exit aperture 206 and out through an exit chute 207 onto a conveyor belt 210. As noted above, the conveyor belt 210 is driven by rotating driving members 212 that drive the conveyor belt 210 in the direction shown. In various embodiments, the speed of the driving members 212 may be adjusted to optimize downstream evaluating and sorting of the seeds 201.

A vision system 214 and sorting system 215 are shown downstream from the bowl 202. As noted above, the vision system 214 comprises an illuminating device, at least one sensing device, and a controller configured to control the illuminating and sensing devices. In the exemplary embodiment, the illuminating device comprises a light source that uses a bulb configured to emit electromagnetic radiation at a wavelength spectrum matched to illuminate the fluorescent protein marker. One exemplary embodiment includes multiple CCD cameras and filters configured to enhance the illumination and to aid in discerning the presence of the marker. The seeds 201 are sorted by the sorting system 215 into "+" containers 216 and "−" containers 218. In the exemplary embodiment, a series of mechanical deflectors are used to the singulated seeds 201 based on the presence or absence of the marker. In the exemplary embodiment, seeds containing the marker are sorted into the "+" containers 216 and seeds that do not contain the marker are sorted into the "−" containers 218. Although not shown in the figure, in other embodiments the seeds 201 contained in the "−" container 218 may be re-routed through the hopper 202 so that these seeds make a successive pass through the system 200. In such a manner any seeds that were not identified as exhibiting the marker may be identified in one or more successive passes through the system 200.

FIG. 5 shows another exemplary system 300 for singulating, evaluating, and sorting seeds based on the presence or absence of a marker in accordance with an embodiment of the present invention. The exemplary embodiment includes a hopper 302 that receives a bulk sample A of seeds and feeds the seeds onto a disk 304. In the exemplary embodiment, the hopper 302 includes a gate 303 that allows a controlled release of a quantity of seeds 301 onto the disk 304 based on gravitational force. The disk 304 is operatively connected to a motor (not shown) through a shaft 305 such that the disk 304 rotates in the direction shown. The disk 304 also includes a series of seed gates 308 that are located along a periphery 306 of the disk 304. The seed gates 308 are configured to receive individual seeds 301 that have been forced toward the periphery 306 of the disk 304 due to centrifugal force caused by the rotation of the disk 304. In the exemplary embodiment, the gates 308 are controllable such that each gate 308 may open to release individual seeds 301. An exit chute 307 is located adjacent the periphery 306 of the disk 304. In the exemplary embodiment, each gate 308 may be individually controlled to open and release an individual seed 301 when the gate 308 is adjacent the exit chute 307. A seed 301 released by a gate 308 when adjacent the exit chute 307 travels through the exit chute 307 and is deposited onto a conveyor belt 310. As noted above, the conveyor belt 310 is driven by rotating driving members 312 that drive the conveyor belt 310 in the direction shown. In various embodiments, the speed of the driving members 312 may be adjusted to optimize downstream evaluating and sorting of the seeds 301. As a result, seeds 301 are singulated along the conveyor belt 310. As similarly described above, a vision system 314 and sorting system 315 are shown downstream from the rotating disk 304 for evaluating and sorting seeds 301 based on the presence or absence of the marker.

FIG. 6 shows yet another exemplary system 400 for singulating, evaluating, and sorting seeds based on the presence or absence of the marker in accordance with an exemplary embodiment of the present invention. In the exemplary embodiment, a hopper 402 is configured to receive a bulk sample A of seeds. The hopper 402 may be vibrating and may include a forward pitch that leads to an opening 403 such that seeds from the bulk sample A leave the opening 403 at a controlled rate. A sloped device 404 is located adjacent the opening 403 of the hopper 402. The sloped device include a first end 405 that is located adjacent the opening 403 of the hopper 402, and a second end 407 that is located a lower elevation than the first end 405. The sloped device of the exemplary embodiment includes at least one groove 406 configured to form a channel that aligns seeds exiting the hopper 402 into a single file row of individual seeds 401. In the exemplary embodiment, the groove 406 is v-shaped, however in other embodiments the groove 406 may be any other shape, such as u-shaped, that is configured to align seeds into a single file row of individual seeds 401. Seeds 401 aligned in the groove 406 of the sloped device 404 are urged toward the second end 407 of the sloped device 404 by gravitational force. A conveyor belt 410 is located below the second end 407 of the sloped device 404 to receive individual seeds 401 that fall by force of gravity from the second end 407 of the sloped device 404. As noted above, the conveyor belt 410 includes rotating driving members 412 that drive the conveyor belt 410 in the direction shown. In various embodiments, the speed of the driving members 412 may be adjusted to optimize downstream evaluating and sorting of the seeds 401. As a result, seeds 401 are singulated along the conveyor belt 410. As similarly described above, although not shown, a vision system and sorting system (see FIG. 8, for example) are located downstream from the sloped device for evaluating and sorting seeds based on the presence or absence of the marker. As described in the Experimental Example herein, a vibratory hopper 402 singulation device, coupled with a Satake ScanMaster® sorting system may result in relatively efficient and accurate sorting results. For example, using such an exemplary system, the sorting step 16 may comprises sorting the seeds at a speed of at least about 500 seeds per minute, and in some embodiments at a speed of at least about 750 seeds per minute.

The foregoing merely illustrates how exemplary embodiments of the present invention distinguish seeds containing a genetic element of interest from a bulk sample. Referring now to FIG. 7, a block diagram of an exemplary electronic device (e.g., PC, laptop, PDA, etc.) configured to execute the method of distinguishing seeds containing a genetic element of interest of exemplary embodiments of the present invention is shown. The electronic device may include various means for performing one or more functions in accordance with exemplary embodiments of the present invention, including those more particularly shown and described herein. It should be understood, however, that the electronic device may include alternative means for performing one or more like functions, without departing from the spirit and scope of the present invention. As shown, the electronic device may generally include means, such as a processor, controller, or the like 740 connected to a memory 742, for performing or controlling the various functions of the entity.

The memory can comprise volatile and/or non-volatile memory, and typically stores content, data or the like. For example, the memory typically stores content transmitted from, and/or received by, the electronic device. Also for example, the memory typically stores software applications, instructions or the like for the processor to perform steps associated with operation of the electronic device in accordance with embodiments of the present invention. In particular, the memory 742 may store computer program code for an application and other computer programs. For example, in one exemplary embodiment of the present invention, the memory may store computer program code for, among other things, evaluating at least some of the seeds of a bulk sample for the presence or absence of a marker associated with at least some seeds containing a genetic element of interest of the bulk sample using an evaluating device, and sorting the seeds containing a genetic element of interest based on the presence or absence of the marker.

In addition to the memory 742, the processor 740 can also be connected to at least one interface or other means for displaying, transmitting and/or receiving data, content or the like. In this regard, the interface(s) can include at least one communication interface 746 or other means for transmitting and/or receiving data, content or the like, as well as at least one user interface that can include a display 748 and/or a user input interface 750. The user input interface, in turn, can comprise any of a number of devices allowing the electronic device to receive data from a user, such as a keypad, a touch display, a joystick or other input device.

As described above and as will be appreciated by one skilled in the art, embodiments of the present invention may be configured as a method and apparatus. Accordingly, embodiments of the present invention may be comprised of various means including entirely of hardware, entirely of software, or any combination of software and hardware. Furthermore, embodiments of the present invention may take the form of a computer program product consisting of a computer-readable storage medium (e.g., the memory 742 of FIG. 16) and computer-readable program instructions (e.g., computer software) stored in the storage medium. Any suitable computer-readable storage medium may be utilized including hard disks, CD-ROMs, optical storage devices, or magnetic storage devices.

Exemplary embodiments of the present invention have been described above with reference to block diagrams and flowchart illustrations of methods, apparatuses (i.e., systems) and computer program products. It will be understood that each block of the block diagrams and flowchart illustrations, and combinations of blocks in the block diagrams and flowchart illustrations, respectively, can be implemented by various means including computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The following Experimental Example is provided only by way of example, and not by way of limitation.

Experimental Example

Introduction

Fluorescent protein (FP) marked seed are being produced for use in sterility systems and for evaluating the impact of one or more inserted genes on yield. It is a laborious process to separate a segregating population of seed into those containing (+) and those not containing (−) a genetic element of interest.

A project was initiated to develop an automated sorting routine that may be capable of efficiently separating FP+ from FP− seed using a vibratory feeder similar to that shown in FIG. 6

Results

A vibratory feeder (see FIG. 6, for example) was evaluated with the Satake ScanMaster® system to assess sorting speed and accuracy in some embodiments of the present invention. It is known that it takes approximately 30 minutes to sort 3500 kernels by hand. The FP-discerning ScanMaster® (see FIG. 8, for example) equipped with a vibratory feeder (see FIG. 6, for example) for singulation, was shown to be capable of sorting the same sample in about 2 to 3 minutes. Thus, the substantially automated method embodiments of the present invention reduced sorting time by approximately 90%. Unfortunately, the ScanMaster® color sorter was only able to remove 90 to 95% of the FP seed from a 50:50 mixture in a single pass. During this process a significant number of FP− seed were comingled with FP+ seed in what should be a pure FP+ sample. This level of performance then suggests that some manual sorting may be required in some method embodiments to achieve a desired level of purity.

For example, if a typical yield trial sample contained 4000 kernels (50% FP− and 50% FP+) it would require about 40 minutes to sort the FP seed. This is a sorting rate of 50 seeds/minute. If the same sample were sorted using substantially automated embodiments of the present invention, it would require less than 30 seconds to generate a 95% pure sample of FP+ seed. For a 2000 kernel FP+ sample, there would be about 100 FP− kernels that would need to be manually removed. If the manual sorting rate is 50 seeds/minute, the actual time to achieve a nearly 100% pure sample of FP+ seed will be about 2 minutes. Furthermore, if a sample is manually sorted while another is being sorted using the FP Sorter the actual sorting time for a sample would be about 2 minutes. This results in a fifteen-fold reduction in time required for separating FP+ seed from FP− seed.

If an automatic re-sort function (i.e. re-routing the sample back through the sorting procedure for one or more additional passes) is used, it may be possible to recover 99% of the FP+ seed from the initial sample without having to manually re-sort the FP− fraction. Such a re-sort process extends the cycle time by 15 seconds for a 500 gram seed sample. Given that it will take 2 minutes to sort the FP+ fraction it may be advantageous to routinely re-sort samples, especially small ones, to recover as much of the FP+ seed as possible.

As noted above, the expression of fluorescent proteins may be non-uniform across the surface area of seeds. As a result, the present invention also provides a method for distinguishing seeds containing a marker associated with genetic element of interest from a bulk sample by using an electromagnetic energy emitting device that is configured to excite a majority of the surface area of the seeds and/or by using an evaluating device that is configured receive emissions from a majority of the surface area of the seeds. FIG. 9 shows a non-limiting schematic of a system incorporating a vacuum drum singulating device, an electromagnetic energy emitting device, and an evaluating device in accordance with one embodiment of the present invention. Specifically, FIG. 9 shows a system 500 that includes an exemplary embodiment of a singulating device comprising a plurality of elongate hollow structures operatively connected to a vacuum source used to singulate seeds from a bulk sample. Specifically, the system 500 of the exemplary embodiment includes a hopper 502 into which a bulk sample A of seeds may be placed. A rotating drum 504 is positioned adjacent the hopper 502. The rotating drum 504 includes a plurality of elongate hollow structures 506 that extend into a substantially hollow interior of the drum 504, which is connected to a vacuum source (not shown). The vacuum source creates a zone of negative pressure within the interior of the drum 504, and as a result, distal ends of the elongate hollow structures 506 create discrete areas of negative pressure. As shown in the figure, the drum 504 rotates adjacent an open end of the hopper 502. The hopper 502 is configured such that seeds are urged toward the open end and adjacent the rotating drum 504. The drum 504 rotates in the direction shown such that the elongate hollow structures 506 pass through a portion of the seeds of the bulk sample A adjacent the drum 504.

As the elongate hollow structures 506 rotate through the bulk sample A, the discrete areas of negative pressure located at the distal ends of the elongate hollow structures 506 attract individual seeds 501. The size of the distal ends of each of the elongate hollow structures 506 is configured such the discrete area of negative pressure at the distal end of each of the hollow structures 506 attracts a single seed 501. As shown in the figure, as the elongate hollow structures 506 rotate through the open end of the hopper 502, individual seeds 501 attach to the distal ends of the elongate hollow structures 506. As the drum 504 continues to rotate in the direction shown, a deflector plate 508 (or alternatively, in some embodiments, a compressed air source configured for detaching individual seeds from the elongate hollow structures 506) deflects the seeds 501 from the distal ends of the elongate hollow structures 506 and onto the conveyor belt 510. In the exemplary embodiment, the deflector plate 508 contacts between the distal ends of the elongate hollow structures 506 and the seeds 501 carried by them so that the area of negative pressure is temporarily blocked, effectively releasing the seeds 501 from the distal ends of the elongate hollow structures 506.

As shown generally in FIG. 9, the system 500 may also include a specialized vision system 554 which, in some embodiments, may comprise: (1) an electromagnetic energy emitting device, such as an illuminating device 554a that emits electromagnetic energy at a particular frequency chosen to illuminate and thereby "excite" a marker, and (2) an evaluating device, such as an image sensing device 554c that may discern seeds expressing the marker. In various embodiments, the present invention may include an electronmagnetic energy emitting device that is configured to excite a majority of the surface area of the seeds and/or an evaluating device that is configured to receive emissions from a majority of the surface area of the seeds. In the depicted embodiment, the system 500 includes a pair of illuminating devices 554c collectively configured to excite a majority of the surface area of the seeds. In such a manner, the image sensing device 554c may evaluate a majority of the surface area of the seeds to determine the presence or absence of a marker.

In the depicted embodiment, image sensing device 554c may be further configured for translating the emission into substantially "white" light. Thus, the image sensing device may assign substantially binary values to each seed based on the presence or absence of the marker wherein seeds containing a genetic element of interest (tagged with the relatively "bright" marker) are marked "positive" (and thereby deflected and/or other wise directed into one or more "+" containers 556. Seeds that do not contain a genetic element of interest, or other particulate debris (which may be translated into a "dark" or "negative" result) may be dropped and/or otherwise directed into one or more "−" containers 558. As shown in FIG. 9, the image sensing device 554c (or other component of a vision system 554 may be in communication with the deflector plate 508, which may also include a guide plate 565 that may rotate for directing the "positive" (i.e. seeds containing a genetic element of interest (which the image sensing device 554c may detect as "white" or "bright" seeds)) into one or more "+" containers 556 in response to a binary positive or "1" signal received from the image sensing device 554c or other processing component of the vision system 554. The guide plate 565 may also be configured for directing the "negative" (i.e. seeds that do not contain a genetic element of interest or particulate debris (which the image sensing device 554c may detect as "dark" seeds)) into one or more "−" containers 558 in response to a binary negative or "0" signal received from the image sensing device 554c or other processing component of the vision system 554.

Many different configurations are possible for distinguishing seeds containing a marker associated with genetic element of interest from a bulk sample by using an electromagnetic energy emitting device that is configured to excite a majority of the surface area of the seeds and/or by using an evaluating device that is configured receive emissions from a majority of the surface area of the seeds. Another non-limiting example is shown generally in FIG. 10, which depicts a sorting system 600 that includes a specialized vision system 654 which, in some embodiments, may comprise: (1) an electromagnetic energy emitting device, such as an illuminating device 654a, that emits electromagnetic energy at a particular frequency chosen to illuminate and thereby "excite" a marker, and (2) an evaluating device, such as an image sensing device 654c that may discern seeds expressing the marker. In the depicted embodiment, the system 600 includes a pair of illuminating devices 654a configured to collectively excite a majority of the surface area of the seeds and a pair of image sensing devices 654c configured to collectively receive emissions from a majority of the surface area of the seeds. In such a manner, the image sensing device 654c may evaluate a majority of the surface area of the seeds to determine the presence or absence of a marker.

As similarly described above, the evaluating device 654c of FIG. 10 (or other component of a vision system 654) may be in communication with a sorting device 655 (which may comprise, for example, a valve device and/or compressed air jet device) configured for directing the "positive" (i.e. seeds containing a genetic element of interest (which the image sensing device 654c may detect as "white" or "bright" seeds)) into one or more "+" containers 656 in response to a binary positive or "1" signal received from the image sensing device 654c or other processing component of the vision system 654. The sorting device 655 may also be configured for directing the "negative" (i.e. seeds that do not contain a genetic element of interest or particulate debris (which the image sensing device 654c may detect as "dark" seeds)) into one or more "−" containers 658 in response to a binary negative or "0" signal received from the image sensing device 654c or other processing component of the vision system 654.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for distinguishing seeds containing a genetic element of interest from a bulk sample, the method comprising:

associating a red fluorescent protein marker with at least some of the seeds of the bulk sample;

evaluating at least some of the seeds of the bulk sample for the presence or absence of the red fluorescent protein marker using a seed color sorter; and sorting the seeds containing a genetic element of interest based on the presence or absence of the red fluorescent protein marker;

wherein the sorting step comprises dispensing the sorted individual seeds into at least one container, the container including seeds having the red fluorescent protein marker present or seeds in which the red fluorescent protein marker is absent, and wherein individual seeds are singulated from the bulk sample using a singulating device prior to said evaluating at least some of the seeds of the bulk sample for the presence or absence of the red fluorescent protein marker, and further comprising associating a plurality of supplemental markers with at least some of the seeds containing a corresponding plurality of additional genetic elements of interest of the bulk sample;

evaluating at least one of the seeds of the bulk sample for the presence or absence of the plurality of supplemental markers using the seed color sorter; and sorting the seeds containing the plurality of additional genetic elements of interest based on the presence or absence of the a plurality of supplemental markers.

2. The method according to claim 1, wherein the plurality of supplemental markers are selected from the group consisting of:

yellow fluorescent proteins;
yellow/orange fluorescent proteins;
orange fluorescent proteins;
orange/red fluorescent proteins;
red/orange fluorescent proteins;
red fluorescent proteins;
cyan fluorescent proteins; and combinations thereof.

3. The method according to claim 1, wherein the sorting step comprises sorting the seeds at a speed of at least about 500 seeds per minute.

4. The method according to claim 1, wherein the sorting step comprises sorting the seeds at a speed of at least about 750 seeds per minute.

5. The method according to claim 1, wherein the red fluorescent protein marker is discernable when excited by a certain energy having a wavelength ranging from substantially about 500 nm to substantially about 580 nm, the certain energy having a peak at substantially about 550 nm.

6. The method according to claim 1, wherein said evaluating step comprises:
   exciting the seeds containing a genetic element of interest with the certain energy; and
   detecting an emission resulting at least in part from the exciting step, the emission having a wavelength ranging from substantially about 500 nm to substantially about 600 nm, the emission having a peak at substantially about 580 nm.

7. The method according to claim 1, wherein the singulating step comprises singulating individual seeds using a plurality of elongate hollow structures operatively connected to a vacuum source.

8. The method according to claim 1, wherein the singulating step comprises receiving the bulk sample in a hopper and vibrating the hopper so as to propel individual seeds along an inclined spiral ramp and through a gap configured to permit the passage of one seed at a time.

9. The method according to claim 1, wherein the singulating step comprises:
   receiving the bulk sample in a hopper;
   feeding seeds from the hopper to a rotatable disk; and
   rotating the rotatable disk so as to distribute the seeds to a periphery of the rotatable disk by application of centrifugal force.

10. The method according to claim 1, wherein the singulating step comprises:
    receiving the bulk sample in a hopper;
    vibrating the bulk sample such that seeds tend to move towards an opening in the hopper;
    distributing seeds from the opening in the hopper to a sloped device that includes at least one groove such that a line of individual seeds is formed in the groove; and
    depositing individual seeds by gravity force from the sloped device onto a conveying device.

11. The method of claim 1, wherein the genetic element of interest comprises male sterility, and wherein the absence of the red fluorescent protein marker indicates male sterility.

12. The method according to claim 1, wherein said evaluating step comprises evaluating seeds for the presence of a marker using at least one image sensing device configured to differentiate between a range of normal seed emissions and an emission from the red fluorescent protein marker.

13. The method according to claim 12, wherein the image sensing device is a CCD device or a CMOS device.

14. The method according to claim 12, wherein the seed color sorter further comprises at least one filter disposed substantially between the image sensing device and the seeds containing a genetic element of interest, the at least one filter configured for passing the emission from the red fluorescent protein marker to the image sensing device.

15. The method according to claim 1, wherein said evaluating step comprises evaluating seeds for the presence of a marker using at least one image sensing device configured to differentiate between a range of normal seed emissions and at least one emission from one or more of the plurality of supplemental markers.

16. The method according to claim 15, wherein the seed color sorter further comprises at least one tunable filter disposed substantially between the image sensing device and the seeds containing a genetic element of interest, the at least one tunable filter configured for selectively passing the at least one emission from one or more of the plurality of supplemental markers to the image sensing device.

17. A computer program product for distinguishing seeds containing a genetic element of interest that have a red fluorescent protein marker associated with at least some of the seeds of a bulk sample, the computer program product comprising a computer-readable storage medium having computer-readable program code instructions stored therein comprising:
    a first set of instructions for evaluating at least some of the seeds of the bulk sample for the presence or absence of the red fluorescent protein marker using a seed color sorter; and
    a second set of instructions for sorting the seeds containing a genetic element of interest based on the presence or absence of the red fluorescent protein marker;
    wherein the second set of instructions comprises instructions for dispensing the sorted individual seeds into at least one container, the container including seeds having the red fluorescent protein marker present or seeds in which the red fluorescent protein marker is absent, and
    further comprising a third set of instructions for controlling a singulating device to singulate individual seeds from the bulk sample prior to evaluating at least some of the seeds of the bulk sample for the presence or absence of the red fluorescent protein marker, and
    wherein at least a portion of the seeds of the bulk sample contain a plurality of additional genetic elements of interest associated with a corresponding plurality of supplemental markers, the computer program product further comprising:
    a fourth set of instructions for evaluating at least one of the seeds of the bulk sample for the presence or absence of the plurality of supplemental markers using the seed color sorter; and
    a fifth set of instructions for sorting the seeds containing the plurality of additional genetic elements of interest based on the presence or absence of the a plurality of supplemental markers.

18. The computer program product according to claim 17, wherein the plurality of supplemental markers are selected from the group consisting of:
    yellow fluorescent proteins;
    yellow/orange fluorescent proteins;
    orange fluorescent proteins;
    orange/red fluorescent proteins;
    red/orange fluorescent proteins;
    red fluorescent proteins;
    cyan fluorescent proteins; and combinations thereof.

19. The computer program product according to claim 17, wherein the second set of computer instructions for sorting comprises sorting the seeds at a speed of at least about 500 seeds per minute.

20. The computer program product according to claim 17, wherein the second set of computer instructions for sorting comprises sorting the seeds at a speed of at least about 750 seeds per minute.

21. The computer program product according to claim 17, wherein said third set of instructions comprises a set of instructions for singulating individual seeds using a plurality of elongate hollow structures operatively connected to a vacuum source.

22. The computer program product according to claim 17, wherein said third set of instructions comprises a set of instructions for receiving the bulk sample in a hopper and vibrating the hopper so as to propel individual seeds along an inclined spiral ramp and through a gap configured to permit the passage of one seed at a time.

23. The computer program product according to claim 17, wherein said third set of instructions comprises:
    a set of instructions for receiving the bulk sample in a hopper, feeding seeds from the hopper to a rotatable disk, and rotating the rotatable disk so as to distribute the seeds to a periphery of the rotatable disk by application of centrifugal force.

24. The computer program product according to claim 17, wherein said third set of instructions comprises:
a set of instructions for receiving the bulk sample in a hopper, vibrating the bulk sample such that seeds tend to move towards an opening in the hopper, distributing seeds from the opening in the hopper to a sloped device that includes at least one groove such that a line of individual seeds is formed in the groove, and depositing individual seeds by gravity force from the sloped device onto a conveying device.

25. The method of claim 17, wherein the genetic element of interest comprises male sterility, and wherein the absence of the red fluorescent protein marker indicates male sterility.

26. The computer program product according to claim 17, wherein the red fluorescent protein marker is discernable when excited by a certain energy having a wavelength ranging from substantially about 500 nm to substantially about 580 nm, the certain energy having a peak at substantially about 550 nm.

27. The computer program product according to claim 26, wherein said first set of instructions comprises:
exciting the seeds containing a genetic element of interest with the certain energy; and
detecting an emission resulting at least in part from the exciting step, the emission having a wavelength ranging from substantially about 500 nm to substantially about 600 nm, the certain energy having a peak at substantially about 580 nm.

28. The computer program product according to claim 17, wherein said first set of instructions comprises evaluating seeds for the presence of a marker using at least one image sensing device configured to differentiate between a range of normal seed emissions and an emission from the red fluorescent protein marker.

29. The computer program product according to claim 28, wherein the image sensing device is a CCD device or a CMOS device.

30. The computer program product according to claim 28, wherein the seed color sorter further comprises at least one filter disposed substantially between the image sensing device and the seeds containing a genetic element of interest, the at least one filter configured for passing the emission from the red fluorescent protein marker to the image sensing device.

31. The computer program product according to claim 17, wherein said third set of instructions comprises evaluating seeds for the presence of a marker using at least one image sensing device configured to differentiate between a range of normal seed emissions and at least one emission from one or more of the plurality of supplemental markers.

32. The computer program product according to claim 31, wherein the seed color sorter further comprises at least one tunable filter disposed substantially between the image sensing device and the seeds containing a genetic element of interest, the at least one tunable filter configured for selectively passing the at least one emission from one or more of the plurality of supplemental markers to the image sensing device.

33. A method for distinguishing seeds containing a genetic element of interest from a bulk sample, the method comprising:
associating a marker with at least some of the seeds of the bulk sample;
exciting the seeds using an electromagnetic energy emitting device;
evaluating at least some of the seeds of the bulk sample for the presence or absence of the marker using a seed color sorter; and
sorting the seeds containing a genetic element of interest based on the presence or absence of the marker;
wherein the sorting step comprises dispensing the sorted individual seeds into at least one container, the container including seeds having a red fluorescent protein marker present or seeds in which a red fluorescent protein marker is absent,
wherein the electromagnetic energy emitting device is configured to excite a majority of the surface area of the seeds,
wherein individual seeds are singulated from the bulk sample using a singulating device prior to said evaluating at least some of the seeds of the bulk sample for the presence or absence of the red fluorescent protein marker, and
further comprising associating a plurality of supplemental markers with at least some of the seeds containing a corresponding plurality of additional genetic elements of interest of the bulk sample;
evaluating at least one of the seeds of the bulk sample for the presence or absence of the plurality of supplemental markers using the seed color sorter; and
sorting the seeds containing the plurality of additional genetic elements of interest based on the presence or absence of the a plurality of supplemental markers.

34. The method of claim 33, wherein the genetic element of interest comprises male sterility, and wherein the absence of the red fluorescent protein marker indicates male sterility.

35. The method according to claim 33, wherein exciting the seeds using an electromagnetic energy emitting device comprises exciting the seeds using at least one illuminating device configured to illuminate a majority of the surface area of the seeds.

36. The method according to claim 35, wherein exciting the seeds using at least one illuminating device further comprises using two or more illuminating devices arranged to collectively illuminate a majority of the surface area of the seeds.

37. The method according to claim 33, wherein evaluating at least some of the seeds of the bulk sample comprises evaluating at least some of the seeds of the bulk sample using at least one image sensing device configured to receive emissions from a majority of the surface area of the seeds.

38. The method according to claim 37, wherein evaluating at least some of the seeds of the bulk sample further comprises using two or more image sensing devices arranged to collectively receive emissions from a majority of the surface area of the seeds.

39. The method according to claim 33, further comprising:
associating one or more supplemental markers with at least some of the seeds containing a corresponding plurality of additional genetic elements of interest of the bulk sample;
evaluating at least one of the seeds of the bulk sample for the presence or absence of the supplemental markers using the seed color sorter; and
sorting the seeds containing the plurality of additional genetic elements of interest based on the presence or absence of the supplemental markers.

40. The method according to claim 39, wherein the marker and the supplemental markers are selected from the group consisting of:
green fluorescent proteins;

green/yellow fluorescent proteins;
yellow fluorescent proteins;
yellow/orange fluorescent proteins;
orange fluorescent proteins;
orange/red fluorescent proteins;
red/orange fluorescent proteins;
red fluorescent proteins;
cyan fluorescent proteins; and combinations thereof.

41. A method for distinguishing seeds containing a genetic element of interest from a bulk sample, the method comprising:
associating a red fluorescent protein marker with at least some of the seeds of the bulk sample;
evaluating at least some of the seeds of the bulk sample for the presence or absence of the red fluorescent protein marker using a seed color sorter; and
sorting the seeds containing a genetic element of interest based on the presence or absence of the red fluorescent protein marker,
wherein the method further comprises re-routing the sorted seeds through the color seed sorter and re-evaluating the sorted seeds for the presence or absence of the red fluorescent protein marker;
wherein individual seeds are singulated from the bulk sample using a singulating device prior to said evaluating at least some of the seeds of the bulk sample for the presence or absence of the red fluorescent protein marker, and
further comprising associating a plurality of supplemental markers with at least some of the seeds containing a corresponding plurality of additional genetic elements of interest of the bulk sample;
evaluating at least one of the seeds of the bulk sample for the presence or absence of the plurality of supplemental markers using the seed color sorter; and
sorting the seeds containing the plurality of additional genetic elements of interest based on the presence or absence of the a plurality of supplemental markers.

42. The method of claim 41 wherein re-routing the sorted seeds through the color seed sorter comprises automatically re-routing the sorted seeds through the color seed sorter.

43. A method for distinguishing seeds containing a genetic element of interest from a bulk sample, the method comprising:
associating a red fluorescent protein marker with at least some of the seeds of the bulk sample;
evaluating at least some of the seeds of the bulk sample for the presence or absence of the red fluorescent protein marker using a seed color sorter; and
sorting the seeds containing a genetic element of interest based on the presence or absence of the red fluorescent protein marker,
wherein the sorting step comprises dispensing the sorted individual seeds into at least one container, the container including seeds having the red fluorescent protein marker present or seeds in which the red fluorescent protein marker is absent,
wherein individual seeds are singulated from the bulk sample using a singulating device prior to said evaluating at least some of the seeds of the bulk sample for the presence or absence of the red fluorescent protein marker, and
wherein the evaluating step comprises exciting the seeds containing a genetic element of interest with a certain energy, detecting an emission resulting at least in part from the exciting step, and translating the emission into substantially white light.

* * * * *